(12) United States Patent
Waga et al.

(10) Patent No.: US 8,203,032 B2
(45) Date of Patent: Jun. 19, 2012

(54) APPLICATION OF FLUORESCENT PROTEIN TO GARDEN PLANT

(75) Inventors: Iwao Waga, Koto-ku (JP); Hiromi Takenaka, Koto-ku (JP); Shu Muto, Koto-ku (JP)

(73) Assignee: NEC Soft, Ltd., Tokyo (JP)

( * ) Notice: Subject to any disclaimer, the term of this patent is extended or adjusted under 35 U.S.C. 154(b) by 493 days.

(21) Appl. No.: 12/374,995

(22) PCT Filed: Jul. 25, 2007

(86) PCT No.: PCT/JP2007/064586
§ 371 (c)(1),
(2), (4) Date: Jan. 23, 2009

(87) PCT Pub. No.: WO2008/013202
PCT Pub. Date: Jan. 31, 2008

(65) Prior Publication Data
US 2010/0043104 A1 Feb. 18, 2010

(30) Foreign Application Priority Data
Jul. 25, 2006 (JP) ................. 2006-201881

(51) Int. Cl.
*C12N 15/82* (2006.01)
*C12N 15/84* (2006.01)
*C12N 15/12* (2006.01)

(52) U.S. Cl. ........ 800/282; 800/288; 800/294; 800/306; 800/317; 800/323.1; 800/323.2

(58) Field of Classification Search ............... None
See application file for complete search history.

(56) References Cited

U.S. PATENT DOCUMENTS
2005/0221338 A1 10/2005 Tsuji et al.

FOREIGN PATENT DOCUMENTS

| WO | 03/018808 A1 | 3/2003 |
|---|---|---|
| WO | 2005/095599 A1 | 10/2005 |
| WO | 2005/100565 A1 | 10/2005 |

OTHER PUBLICATIONS

Locus AB185173 (May 2006).*
Harper et al. Nature Biotechnology 17(11): 1125-1129 (Nov. 1999).*
Masuda, H. et al., "A novel yellowish-green fluorescent protein from the marine copepod", Gene, May 10, 2006, pp. 18-25, vol. 372.
Mercuri, A. et al., "Green Fluorescent Flowers", Plant Science, 2001, pp. 961-968, vol. 161.
Ishida, A. et al., "Production of Transgenic Japanese Morning Glory (*Pharbitis nil*) with New Fluorescent Protein Genes", Res. Bull. Aichi. Agric. Res. Ctr., 2005, pp. 141-146, vol. 37.
Azpiroz-Leehan, R. et al., "T-DNA insertion mutagenesis in *Arabidopsis* going back and forth", Trends in Genetics, Apr. 1997, pp. 152-156, vol. 13, No. 4, Elsevier Science Ltd.
Seki, M. et al., "Functional Annotation of a Full-Length *Arabidopsis* cDNA Collection", Science, Apr. 2002, pp. 141-145, vol. 296, No. 5565, American Association for the Advancement of Science.
Taji, T. Et al., "Important roles of drought- and cold-inducible genes for galactinol synthase in stress tolerance in *Arabidopsis thaliana*", The Plant Journal, Feb. 2002, pp. 417-426, vol. 29, No. 4, Blackwell Publishing.
Sanders, P.R. et al., "Comparision of cauliflower mosaic virus 35S and nopaline synthase promoters in transgenic plants", Nucleic Acids Research, Feb. 1987, pp. 1543-1558, vol. 15, No. 4, IRL Press.
C.N. Stewart Jr. "The utility of green fluorescent protein in transgenic plants" Plant Cell Reports, vol. 20, No. 5, Jul. 5, 2001, pp. 376-382, XP002549328.

* cited by examiner

*Primary Examiner* — David T Fox
(74) *Attorney, Agent, or Firm* — Sughrue Mion, PLLC

(57) ABSTRACT

The present invention provides a process for generation of a transformed plant capable of emitting fluorescence by introducing a gene encoding a non-plant-derived fluorescent protein into a plant such that the fluorescent protein is recombinantly expressed in the active form of its mature protein in the leaf or petal of the plant, and also provides a transformed garden plant capable of emitting fluorescence that is generated by using the process. For example, cDNA encoding the full-length amino acid sequence of a *Chiridius poppei*-derived fluorescent protein CpYGFP or its H52F modified protein CpYGFP H52F is inserted into a T-DNA-based expression vector system, which is in turn introduced into the chromosomal DNA of a plant. As a result, the transformed plant thus generated can exhibit fluorescence attributed to these fluorescent proteins and exhibit no substantial difference in the other phenotypes from wild-type one of the plant.

16 Claims, 11 Drawing Sheets
(5 of 11 Drawing Sheet(s) Filed in Color)

Fig. 8
(a)
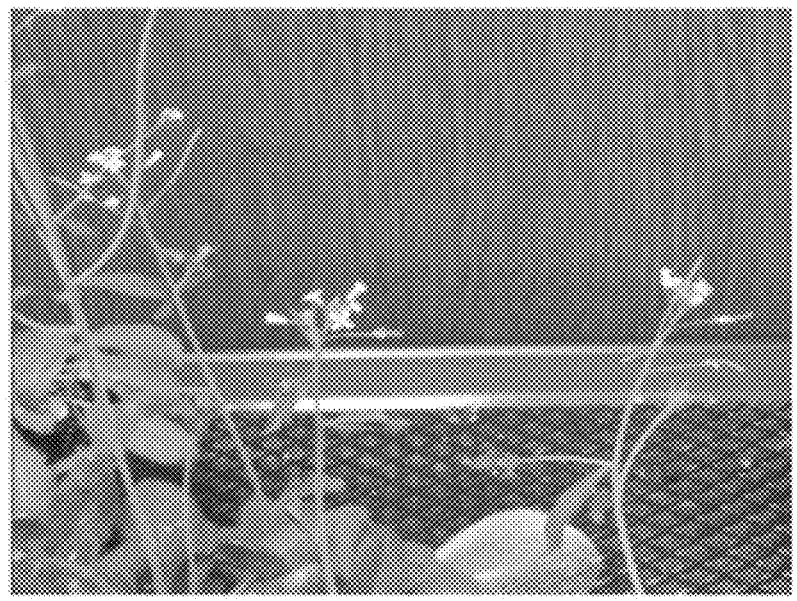
(b)
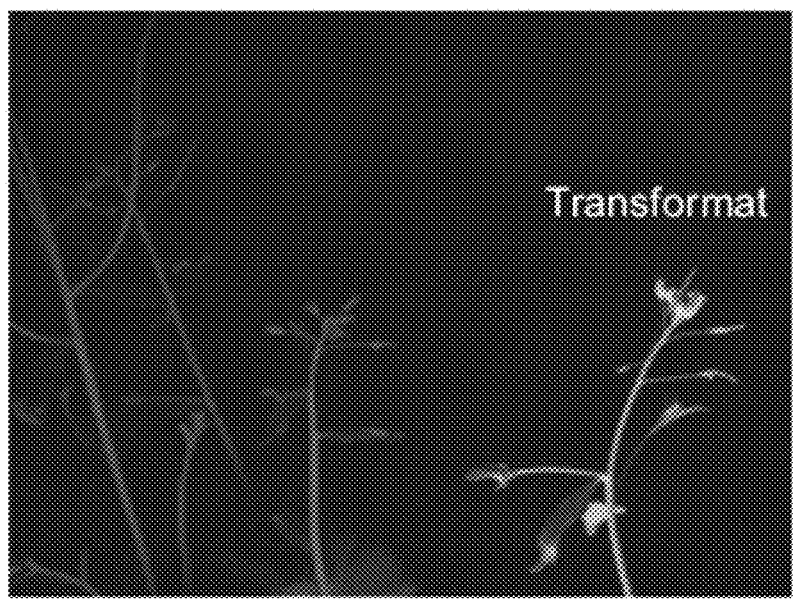

Fig. 9
(a)
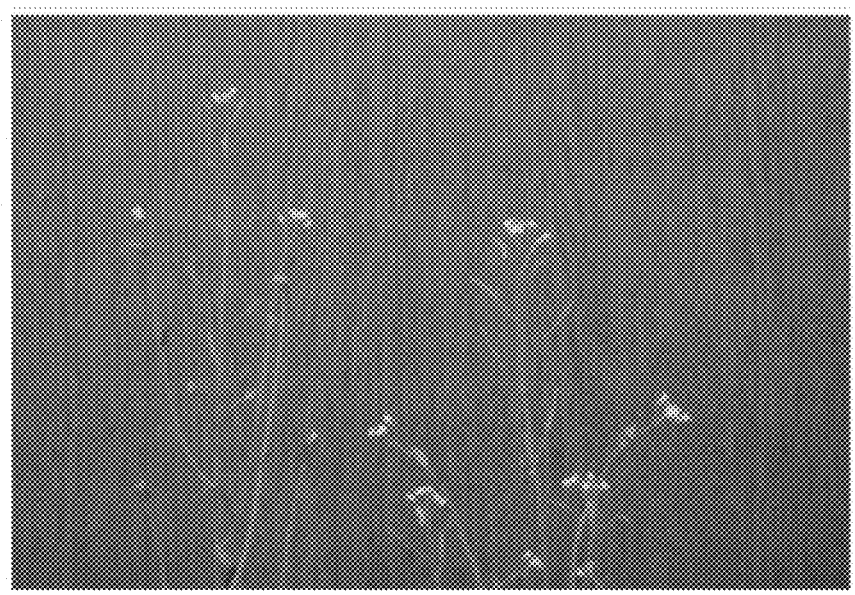
(b)

Fig. 10

```
                                    10              20              30
→  CpGFP      - - - - - - - - M T T F K I E S R I H G N L N G E K F E L V G G G V G E - E - G R L
   DsRed      M R S S K N V I K E F M R F K V R M E G T V N G H E F E I E G E G E G R P Y E G H N
   aqGFP      M S K G E E L F T G V V P I L V E L D G D V N G H K F S V S G E G E G D A T Y G K L
                              b₁ 4-14                          b₂ 17-28

40              50              60              70              80
   E I E M K T K D K - P L A F S P F L L S H C M G Y G F Y H F A S F P K G T K - - N I Y L H A A T N G G
   T V K L K V T K G G P L P F A W D I L S P Q F Q Y G S K V Y V K H P A D I P - - D Y K K L S F P E - G
   T L K F I C T T G - K L P V P W P T L V T T F S Y G V Q C F S R Y P D H M K R H D F F K S A M P E - G
       b₃ 31-39                                                bx 90              100             110             120             130
   Y T N T R K E I Y E D G G I L E V N F R Y T Y E F N K I I G D V E C I G H G F P S Q S P I F K D T I V
   F K W E R V M N F E D G G V V T V T Q D S S L Q D G C F I Y K V K F I G V N F P S D G P V M Q K K T M
   Y V Q E R T I F F K D D G N Y K T R A E V K F E G D T L V N R I E L K G I D F K E D G N I L G H K L E
             b₄ 80-89           b₅ 93-104           b₆ 107-117

140             150             160             170
   - K S C P T V D L M L P M S - G N I I A S S Y A R A F Q L K D G S F Y T A E V K N N I D F K - - - N P
   - G W E A S T E R L Y P R D - - G V L K G E I H K A L K L K D G G H Y L V E F K S I Y M A K - - K P V
   Y N Y N S H N V Y I M A D K Q K N G I K V N F K I R H N I E D G S V Q L A D H Y Q Q N T P I G D G P V
             b₇ 132-143             b₈ 147-158           b₉ 162-174

180             190             200             210             220
   I H E S F S K S G P M F T H R R V E E T - H T - - - K E N L A M V E Y Q Q V F N S A P R D M - - - -
   Q L - - P G - - - Y Y Y V D S K L D I T S H N E D - Y T I V E Q Y E R T E G R H H L F L - - - - - -
   L L - - P D - - - N H Y L S T Q S A L S K D P N E K R D H M V L L E F V T A A G I T H G M D E L Y K
                       b₁₀ 188-199                      b₁₁ 202-212
```

APPLICATION OF FLUORESCENT PROTEIN TO GARDEN PLANT

The instant application is a 371 of PCT/JP2007/064586 filed Jul. 25, 2007, the disclosure of which is incorporated herein by reference.

TECHNICAL FIELD

The present invention relates to a process for generation of a garden plant capable of emitting fluorescence that is attributed to a marine zooplankton-derived fluorescent protein in each tissue of the adult plant by the recombinant expression of the fluorescent protein, and to a garden plant prepared by the process.

BACKGROUND ART

An approach of introducing a foreign gene using an *Agrobacterium*-derived plasmid has been known widely as one of processes for generating a transformed plant by introducing a foreign gene, in such a case when a target plant undergoes infection with the pathogenic bacterium *Agrobacterium* (cancer bacterium). A Ti-plasmid (Tumor inducing plasmid) from *Agrobacterium tumefaciens* or a Ri-plasmid from *Agrobacterium rhizogenes* has been studied widely as the *Agrobacterium*-derived plasmid that can be used in genetic recombination. These *Agrobacterium*-derived plasmids, Ti- and Ri-plasmids, contain a region called T-DNA. This T-DNA region is incorporated into plant chromosomes. Moreover, gene clusters involved in the incorporation of the T-DNA region into plant chromosomes are present in a Vir region in proximity to the T-DNA region. The Vir region contains VirA, VirB, VirC, VirD, VirE, and VirG genes, and products thereof have been understood to promote the introduction of the T-DNA region into plant chromosomes.

The T-DNA region is approximately 20 kb in size. Although the structure of the region differs among species, 25-base-pair sequences at both ends of this T-DNA region are similar among species and essential for the incorporation of T-DNA into chromosomal DNA. A gene of interest is inserted into a site flanked by the 25-base-pair sequences (border nucleotide sequences) at both ends of the T-DNA region. The modified Ti-plasmid is introduced into *Agrobacterium* to generate a transformant. A target plant is infected with this transformant such that the T-DNA region comprising the insert of the gene of interest is introduced into the chromosomal DNA of the target plant with high efficiency.

A gene encoding a *Bacillus thuringiensis*-derived insecticidal protein (BT-toxin) has been introduced into the chromosomal DNA of a *Nicotiana tabacum* cell by using the Ti-plasmid system via infection with an *Agrobacterium* transformant to generate a transformed plant that recombinantly expresses the BT-toxin therein. Furthermore, a gene encoding firefly-derived luminescent protein (luciferase) has been introduced into the chromosomal DNA of a *Nicotiana tabacum* cell by using the Ti-plasmid system to generate a transformed plant that expresses an active luciferase therein.

It has been reported that the introduction of T-DNA into the chromosomal DNA of a target plant using a Ti-plasmid system via infection with an *Agrobacterium* transformant usually takes place with frequency on the order of 1 to 2 copies per plant individual (see Non-Patent Document 1: Azpiroz-Leehan, R. et al., Trends Genet., 13 (4), p. 152-6 (1997)). Moreover, the introduction of T-DNA into chromosomal DNA is due to such a mechanism of homologous replacement-based DNA insertion using the 25-base-pair sequences at both ends of the T-DNA region. Accordingly, a T-DNA fragment can be inserted at random into a large number of sites having a nucleotide sequence that permits the homologous replacement-based DNA insertion, which are present in the chromosomal DNA of the target plant. The fact that the introduction of T-DNA usually takes place with frequency on the order of 1 to 2 copies per plant individual means that the insertion of T-DNA takes place only at one site, or two sites at most, of the large number of sites that permit insertion, per plant individual.

Such adavantage that the introduction of T-DNA usually takes place with frequency on the order of 1 to 2 copies per plant individual has been employed profitably to develop a Fox-hunting system (full-length cDNA over-expression gene hunting system) (see Patent Document 1: pamphlet of WO 03/018808 and Non-Patent Document 2: Seki M., et al., Science Vol. 296, No. 5565, p. 141-145 (2002)). In a recombinant expression vector system used in the Fox-hunting system, a T-DNA region thereof, which is finally introduced into the chromosomal DNA of the plant, comprises:

as regulatory sequences for the expression of an inserted gene, a "cassette" comprising a combination of a promoter sequence that induces expression in a target plant and a terminator sequence that terminates transcription; and a cloning site for inserting full-length cDNA derived from the gene to be inserted, which is provided downward of the promoter sequence and upward of the terminator sequence. An *E. coli*/Agrobacterium binary vector, for example, pTAS- or pBig-derived vector, is used, which comprises said T-DNA region and a Ti-plasmid-derived replication origin (ORI) and is additionally equipped with a selection marker gene such as an antibiotic resistance gene and further with an *E. coli* plasmid-derived replication origin (ORI). The full-length cDNA derived from the gene to be introduced is inserted using the cloning site in the binary vector to construct a vector for transformation, which vector is in turn introduced into *Agrobacterium* having a Ti-plasmid to prepare an *Agrobacterium* transformant. A target plant is infected with this *Agrobacterium* transformant using, for example, a floral dipping method, such that the T-DNA region in the binary vector retained in the transformant is introduced into the chromosomal DNA of the target plant. Each plant individual that has undergone the dipping treatment is subjected to self-pollination, and then a T1 seed is harvested from the plant individual. The T-DNA is inserted only with frequency on the order of 1 to 2 copies in the chromosomal DNA of the target plant. Therefore, when pollen or ovule cells having each n chromosome are formed from 2n homologous chromosomes (a*/a type) by meiosis, the ratio between pollen or ovule cells (a* type) in which the T-DNA has been introduced and pollen or ovule cells (a type) in which the T-DNA has not been introduced is almost equal in number. Accordingly, among T1 seeds, those retaining the T-DNA introduced in the chromosomal DNA (a*/a type or a*/a* type) and those not retaining the T-DNA (a/a type) coexist according to the Mendel's laws of heredity. Whether or not the T-DNA region is actually retained in the chromosomal DNA is confirmed by germinating the harvested T1 seed on, for example, a selective medium supplemented with a drug, and performing primary screening based on the presence or absence of expression of the marker gene such as a drug resistance gene equipped in advance to the T-DNA region to select a transformed plant, in which the T-DNA region has been introduced.

Furthermore, the germinated seed selected by primary screening is grown, and the plant grown therefrom is subjected to phenotypic screening for selecting a transformed plant that exhibits difference in phenotype, which is associated with the expression of the gene inserted in the T-DNA region, in comparison with that of a wild-type plant. For the transformed plant selected in this phenotypic screening, a PCR product derived from the T-DNA region is prepared using a PCR method to verify that the T-DNA region comprising the insert of the full-length cDNA derived from the gene to be introduced is indeed present in the chromosomal DNA thereof. Moreover, each individual of the verified transformed plant selected in phenotypic screening is subjected to self-pollination, and then a T2 seed is harvested from the plant individual.

The approach for preparing a transformed plant using the T-DNA recombinant expression vector system, which has been employed in the Fox-hunting system, can be applied to various plants which are capable of undergoing *Agrobacterium* infection and producing a harvestable T1 seed through the self-pollination of each plant individual.

The plants to which the approach can be applied includes plants belonging to the family Brassicaceae, Poaceae, Soianaceae, or Leguminosae, for instance, a typical example thereof includes the following plants:
the family Brassicaceae: *Arabidopsis thaliana*
the family Solanaceae: *Nicotiana tabacum*
the family Poaceae: *Zea mays, Oryza sativa*
the family Leguminosae: *Glycine max.*

Patent Document 1: WO 03/018808 A1
Non-Patent Document 1: Azpiroz-Leehan, R. et al., Trends Genet., 13 (4), p. 152-6 (1997)
Non-Patent Document 2: Seki M., et al., Science Vol. 296, No. 5565, p. 141-145 (2002)

DISCLOSURE OF THE INVENTION

Problems to be Solved by the Invention

It has been reported that the recombination technique of genetic engineering was applied to change the petal color of a garden plant *Petuniaxhybrida*. In the process, a gene encoding a *Zea mays*-derived enzyme protein was introduced into a *Petuniaxhybrida* species having pale pink petals, which is due to deficiency in an enzyme protein involved in pigment production, to generate such species having vivid red petals, in which the enzyme protein was recombinantly expressed to impart the ability to produce a pigment thereto. Moreover, the aforementioned gene encoding the firefly-derived luminescent protein (luciferase) has been introduced into the chromosomal DNA of a *Nicotiana tabacum* cell using a Ti-plasmid system to transform the cells, and then a plant was regenerated therefrom to create a transformed plant that is capable of expressing an active luciferase therein. This transformed plant of *Nicotiana tabacum* is allowed to absorb, through the root thereof, a solution containing a substrate luciferin dissolved therein such that the recombinantly expressed luciferase acts on the substrate luciferin supplied to each tissue cell in the root, stem, and leaf of the plant. As a result, the plant emits light through chemiluminescence. This plant is called firefly grass, because its luminescence exhibits a tone similar to that of firefly luminescence.

As described above, there have been already reported the cases where the recombination technique of genetic engineering was applied to such an attempt to produce a pigment that is not originally produced by a garden plant or to impart the ability to emit light that is not originally possessed by a plant. In addition to those, the attempts to impart a new visual feature to a garden plant intended as an ornamental plant include a try to impart capability of emitting fluorescence thereto.

The present invention has been achieved for solving said problems, and an object of the present invention is to newly provide a process for generation of a transformed plant capable of emitting fluorescence by introducing a gene encoding a non-plant-derived fluorescent protein into a plant such that the fluorescent protein is recombinantly expressed in the active form of mature protein in the leaf or petal of the plant, and to provide a transformed garden plant capable of emitting fluorescence generated by the process.

Means for Solving the Problems

The present inventors have targeted a garden plant, particularly, a plant that exhibits a green leaf color, and aimed to generate a transformed garden plant capable of emitting fluorescence, which uses fluorescence emitted from a non-plant-derived fluorescent protein recombinantly expressed in the epidermal cell of the leaf thereof. The present inventors have noticed that in the garden plant, a factor responsible for the green color exhibited by the epidermis of the leaf thereof is attributed to the presence of chloroplast in the epidermal cell. Specifically, a large amount of chlorophyll, in addition to yellow carotenoid, is stored in thylakoid present in the chloroplast. The present inventors have noticed that the exhibited green color is attributed to this chlorophyll. In the garden plant that exhibits a green leaf color, the chlorophyll component is composed mainly of chlorophyll a and chlorophyll b. These chlorophylls a and b have the absorption maximum in red and blue-violet regions and can absorb little light in the range of wavelengths 600 nm to 490 nm between these two absorption bands. The present inventors have noticed that as a result of this, the leaf thereof appears green.

The inventors have found out that, at least, in the case when fluorescence emitted from a non-plant-derived fluorescent protein recombinantly expressed in the epidermal cell of the green leaf is used, a peak wavelength $\mu_{em}$ of the fluorescence spectrum of this fluorescent protein as well as a peak wavelength $\lambda_{ex}$ of the wavelength distribution of excitation light (excitation spectrum) that causes the fluorescence needs to exist in the range of the wavelength regions 600 nm to 490 nm. Specifically, if the peak wavelength $\lambda_{ex}$ of the excitation spectrum exhibited by the intended fluorescent protein overlaps with the absorption band of the blue-violet region due to chlorophyll a and chlorophyll b excitation light exposed to the surface of the green leaf is absorbed by the chlorophyll a and chlorophyll b present in large amounts, and as a result, the portion of light that reaches the intended fluorescent protein is reduced down to a low level.

Likewise, if the peak wavelength $\lambda_{em}$ of the fluorescence spectrum exhibited by the intended fluorescent protein overlaps with the center of the absorption band of the red region due to chlorophyll a and chlorophyll b, the emitted fluorescence is absorbed by the chlorophyll a and chlorophyll b present in large amounts. As a result, the intensity of the fluorescence emitted from the surface of the green leaf is reduced.

In particular, the inventors have found out that in such a case when fluorescence emitted from a non-plant-derived fluorescent protein recombinantly expressed in the epidermal cell of the green leaf is used, the peak wavelength $\lambda_{em}$ of the fluorescence spectrum of this fluorescent protein is preferably located in the range of 510 nm to 550 nm, and the peak wavelength $\lambda_{ex}$ of the wavelength distribution of excitation light (excitation spectrum) that causes the fluorescence is preferably located at an wavelength longer than 490 nm, particularly, at a wavelength longer than 500 nm. The present inventors have found that a *Chiridius poppei*-derived GFP-like fluorescent protein (CpYGFP) already disclosed in Patent Documents (WO 2005/095599 A1 and U.S. 2005/0221338 A1) can be used preferably as the non-plant-derived fluorescent protein that satisfies the requirements. In addition, the inventors have confirmed that the fluorescent protein CpYGFP is capable of being recombinantly expressed in the epidermal cell of a plant leaf and actually achieves "proper protein folding" and "fluorophore formation" in the plant cell post to translation into a peptide chain. Specifically, according to an approach disclosed in WO 03/018808 A1, cDNA encoding the full-length amino acid sequence of the fluorescent protein CpYGFP is inserted into a T-DNA-based expression vector system, which is in turn introduced into the chromosomal DNA of a plant. As a result, the inventors have confirmed that fluorescence due to the production of mature CpYGFP is observed in the epidermal cell of the plant leaf. In addition, cDNA encoding the full-length amino acid sequence of a H52F modified protein CpYGFP H52F modified from the fluorescent protein CpYGFP by substituting His$^{52}$ by Phe is also inserted into a T-DNA-based expression vector system, which is in turn introduced into the chromosomal DNA of a plant. As a result, the inventors have confirmed that fluorescence due to the production of mature CpYGFP is observed in the epidermal cell of the plant leaf.

In addition to these findings, the present inventors have confirmed that a transformed plant generated by inserting cDNA encoding the full-length amino acid sequence of the *Chiridius poppei*-derived fluorescent protein CpYGFP or its H52F modified protein CpYGFP H52F into a T-DNA-based expression vector system and introducing the T-DNA-based expression vector system into the chromosomal DNA of a plant can exhibit no substantial difference in phenotype from wild-type one of the plant except that it exhibits fluorescence due to these fluorescent proteins. Consequently, the present inventors have completed the present invention.

Specifically, use of a *Chiridius poppei*-derived fluorescent protein according to the present invention is
use of a *Chiridius poppei*-derived fluorescent protein for generation of a transformed plant capable of emitting fluorescence, characterized in that
said *Chiridius poppei*-derived fluorescent protein used therefor is
a *Chiridius poppei*-derived wild-type fluorescent protein CpYGFP comprising the following amino acid sequence (SEQ ID NO: 1):

```
MTTFKIESRI HGNLNGEKFE LVGGGVGEEG RLEIEMKTKD KPLAFSPFLL SHCMGYGFYH    60

FASFPKGTKN IYLHAATNGG YTNTRKEIYE DGGILEVNFR YTYEFNKIIG DVECIGHGFP   120

SQSPIFKDTI VKSCPTVDLM LPMSGNIIAS SYARAFQLKD GSFYTAEVKN NIDFKNPIHE   180

SFSKSGPMFT HRRVEETHTK ENLAMVEYQQ VFNSAPRDM                         219
``` as its full-length amino acid sequence, or
a *Chiridius poppei*-derived modified fluorescent protein CpYGFP H52F comprising the following amino acid sequence (SEQ ID NO: 3):

```
MTTFKIESRI HGNLNGEKFE LVGGGVGEEG RLEIEMKTKD KPLAFSPFLL SFCMGYGFYH    60

FASFPKGTKN IYLHAATNGG YTNTRKEIYE DGGILEVNFR YTYEFNKIIG DVECIGHGFP   120

SQSPIFKDTI VKSCPTVDLM LPMSGNIIAS SYARAFQLKD GSFYTAEVKN NIDFKNPIHE   180

SFSKSGPMFT HRRVEETHTK ENLAMVEYQQ VFNSAPRDM                         219
``` as its full-length amino acid sequence,
a wild-type plant used in the process for generation of the aimed transformed plant capable of emitting fluorescence is a plant which is capable of undergoing *Agrobacterium* infection and producing a harvestable T1 seed through the self-pollination of each plant individual, and
the process for generation of the aimed transformed plant capable of emitting fluorescence comprises steps of:

inserting a DNA fragment encoding the full-length amino acid sequence of the *Chiridius poppei*-derived fluorescent protein into the cloning site of a T-DNA-based binary vector;

introducing the obtained T-DNA-based binary vector into a host bacterium of the genus *Agrobacterium* such that the bacterium of the genus *Agrobacterium* is transformed therewith;

infecting the wild-type plant with the obtained transformant of the bacterium of the genus *Agrobacterium* such that a T-DNA region contained in the T-DNA-based binary vector is recombinantly introduced in the chromosomal DNA of the wild-type plant to obtain a transformed plant;

subjecting each individual of the obtained transformed plant to self-pollination, and then harvesting a T1 seed from the plant individual; and sowing the obtained T1 seed and screening each grown plant to select a transformed plant individual to which a fluorescent phenotype attributed to the recombinant expression of the fluorescent protein in the leaf surface of the plant has been imparted.

In the case where the *Chiridius poppei*-derived fluorescent protein used therefor is the *Chiridius poppei*-derived wild-type fluorescent protein CpYGFP comprising the following amino acid sequence (SEQ ID NO: 1):

```
MTTFKIESRI HGNLNGEKFE LVGGGVGEEG RLEIEMKTKD KPLAFSPFLL SFCMGYGFYH    60

FASFPKGTKN IYLHAATNGG YTNTRKEIYE DGGILEVNFR YTYEFNKIIG DVECIGHGFP   120

SQSPIFKDTI VKSCPTVDLM LPMSGNIIAS SYARAFQLKD GSFYTAEVKN NIDFKNPIHE   180

SFSKSGPMFT HRRVEETHTK ENLAMVEYQQ VFNSAPRDM                         219
``` as a full-length amino acid sequence,
it is preferable that
the DNA fragment encoding the full-length amino acid sequence of the *Chiridius poppei*-derived fluorescent protein should comprise the following nucleotide sequence (SEQ ID NO: 2)

```
ATG AGA ACC TTC AAA ATC GAG TCC CGG ATC CAT GGC AAC CTC AAC GGG    48
GAG AAG TTC GAG TTG GTT GGA GGT GGA GTA GGT GAG GAG GGT CGC CTC    96
GAG ATT GAG ATG AAG ACT AAA GAT AAA CCA CTG GCA TTC TCT CCC TTC   144
CTG CTG TCC CAC TGC ATG GGT TAC GGG TTC TAC CAC TTC GCC AGC TTC   192
CCA AAG GGG ACT AAG AAC ATC TAT CTT CAT GCT GCA ACA AAC GGA GGT   240
TAC ACC AAC ACC AGG AAG GAG ATC TAT GAA GAC GGC GGC ATC TTG GAG   288
GTC AAC TTC CGT TAC ACT TAC GAG TTC AAC AAG ATC ATC GGT GAC GTC   336
GAG TGC ATT GGA CAT GGA TTC CCA AGT CAG AGT CCG ATC TTC AAG GAC   384
ACG ATC GTG AAG TCG TGT CCC ACG GTG GAC CTG ATG TTG CCG ATG TCC   432
GGG AAC ATC ATC GCC AGC TCC TAC GCT AGA GCC TTC CAA CTG AAG GAC   480
GGC TCT TTC TAC ACG GCA GAA GTC AAG AAC AAC ATA GAC TTC AAG AAT   528
CCA ATC CAC GAG TCC TTC TCG AAG TCG GGG CCC ATG TTC ACC CAC AGA   576
CGT GTC GAG GAG ACT CAC ACC AAG GAG AAC CTT GCC ATG GTG GAG TAC   624
CAG CAG GTT TTC AAC AGC GCC CCA AGA GAC ATG TAG                   660
``` as the nucleotide sequence of an open-reading frame encoding the full-length amino acid sequence.

Alternatively, in the case where the *Chiridius poppei*-derived fluorescent protein used therefor is the *Chiridius poppei*-derived modified fluorescent protein CpYGFP H52F comprising the following amino acid sequence (SEQ ID NO: 3):

```
MTTFKIESRI HGNLNGEKFE LVGGGVGEEG RLEIEMKTKD KPLAFSPFLL SFCMGYGFYH    60
FASFPKGTKN IYLHAATNGG YTNTRKEIYE DGGILEVNFR YTYEFNKIIG DVECIGHGFP   120
SQSPIFKDTI VKSCPTVDLM LPMSGNIiAS SYARAFQLKD GSFYTAEVKN NIDFKNPIHE   180
SFSKSGPMFT HRRVEETHTK ENLAMVEYOQ VFNSAPRDM                         219
``` as its full-length amino acid sequence,
it is preferable that
the DNA fragment encoding the full-length amino acid sequence of the *Chiridius poppei*-derived fluorescent protein comprises the following nucleotide sequence (SEQ ID NO: 4):

```
ATG ACA ACC TTC AAA ATC GAG TCC CGG ATC CAT GGC AAC CTC AAC GGG    48
GAG AAG TTC GAG TTG GTT GGA GGT GGA GTA GGT GAG GAG GGT CGC CTC    96
GAG ATT GAG ATG AAG ACT AAA GAT AAA CCA CTG GCA TTC TCT CCC TTC   144
CTG CTG TCC TTC TGC ATG GGT TAC GGG TTC TAC CAC TTC GCC AGC TTC   192
CCA AAG GGG ACT AAG AAC ATC TAT CTT CAT GCT GCA ACA AAC GGA GGT   240
TAC ACC AAC ACC AGG AAG GAG ATC TAT GAA GAC GGC GGC ATG TTG GAG   288
GTC AAC TTC CGT TAC ACT TAC GAG TTC AAC AAG ATC ATC GGT GAC GTC   336
GAG TGC ATT GGA CAT GGA TTC CCA AGT CAG AGT CCG ATC TTC AAG GAC   384
```

```
ACG ATC GTG AAG TCG TGT CCC ACG GTG GAC CTG ATG TTG CCG ATG TCC    432

GGG AAC ATC ATC GCC AGC TCC TAC GCT AGA GCC TTC CAA CTG AAG GAC    480

GGC TCT TTC TAC ACG GCA GAA GTC AAG AAC AAC ATA GAC TTC AAG AAT    528

CCA ATC CAC GAG TCC TTC TCG AAG TCG GGG CCC ATG TTC ACC CAC AGA    576

CGT GTC GAG GAG ACT CAC ACC AAG GAG AAC CTT GCC ATG GTG GAG TAC    624

CAG CAG GTT TTC AAC AGC GCC CCA AGA GAC ATG TAG                    660
``` as the nucleotide sequence of an open-reading frame encoding the full-length amino acid sequence.

On the other hand, it is preferable that any plant belonging to the family Brassicaceae, Poaceae, Solanaceae, or Leguminosae should be selected as the wild-type plant used in the process for generation of the aimed transformed plant capable of emitting fluorescence.

For example, any of the following plants may be selected as the wild-type plant used in the process for generation of the aimed transformed plant capable of emitting fluorescence:
the family Brassicaceae: *Arabidopsis thaliana*,
the family Solanaceae: *Nicotiana tabacum*,
the family Poaceae: *Zea mays, Oryza sativa*, and
the family Leguminosae: *Glycine max*

Furthermore, among variety of garden plants, the following plants:
a rose: the family Rosaceae, the genus *Rosa*;
*Dianthus caryophyllus*: the family Caryophyllaceae, the genus *Dianthus*;
a chrysanthemum, particularly, a cultivated chrysanthemum (*Chrysanthemum morifolium*): the family Compositae, the genus *Chrysanthemum*;
*Gerbera* cvs.: the family Compositae, the genus *Gerbera*;
*Eustoma grandiflorum*: the family Gentianaceae, the genus *Eustoma*;
*Petuniaxhybrida*: the family Solanaceae, the genus *Petunia*;
*Torenia fournieri*: the family Scrophulariaceae, the genus *Torenia*;
*Nierembergia hippomanica*: the family Solanaceae, the genus *Nierembergia*;
garden verbena: the family Verbenaceae, the genus *Verbena*;
*Calibrachoa* hybrid Cultivar: the family Solanaceae, the genus *Calibrachoa*;
*Cyclamen persicum*: the family Primulaceae, the genus *Cyclamen*;
Cactaceae, for example,
the family Cactaceae, the genera *Austrocylindropuntia, Astrophytum, Echinocactus, Echinocereus, Echinopsis, Epiphyllum, Opuntia, Schlumbergera, Chamaecereus, Cylindropuntia, Gymnocalycium, Zygocactus, Selenicereus, Tephrocactus, Neobuxbaumia, Neoraimondia, Nopalea, Ferocactus, Mammillaria, Melocactus, Rhipsalis, Roseocactus,* and *Lophosphora*; and
an orchid, for example,
*Phalaenopsis* cvs.: the family Orchidaceae, the genus *Phalaenopsis*;
*Cymbidium* cvs.: the family Orchidaceae, the genus *Cymbidium*;
*Dendrobium nobile* hybrids, *D. phalaenopsis* hybrids: the family Orchidaceae, the genus *Dendrobium*;
*Oncidium* cvs.: the family Orchidaceae, the genus *Oncidium*; and
*Cattleya* cvs.: the family Orchidaceae, the genus *Cattleya* can be exemplified as the plant which is capable of undergoing infection with the transformed bacterium obtained by introducing the T-DNA-based binary vector into a host bacterium of the genus *Agrobacterium*, and generating a transformed plant. Any of these plants may be selected as the wild-type plant used in the process for generation of the aimed transformed plant capable of emitting fluorescence.

Moreover, it is preferable that *Agrobacterium tumefaciens* is selected as the host bacterium of the genus *Agrobacterium* used in the step of introducing the obtained T-DNA-based binary vector into the host bacterium of the genus *Agrobacterium* such that the bacterium of the genus *Agrobacterium* is transformed therewith. For example, it is preferable that an electro-competent cell of an *Agrobacterium* GV3101 strain is selected as the host bacterium of the genus *Agrobacterium*.

Furthermore, it is preferable that an *E. coli/Agrobacterium* binary vector pBig2113SF is selected as the T-DNA-based binary vector used in the step of inserting a DNA fragment encoding the full-length amino acid sequence of the *Chiridius poppei*-derived fluorescent protein into the cloning site of the T-DNA-based binary vector.

Moreover, the present invention also provides the invention of a process for generation of a transformed plant capable of emitting fluorescence by using a *Chiridius poppei*-derived fluorescent protein which is recombinantly expressed by genetic recombination and intracellularly produced, specifically, the process for generation of the transformed plant capable of emitting fluorescence according to the present invention is a process for generation of a transformed plant capable of emitting fluorescence by using a *Chiridius poppei*-derived fluorescent protein which is recombinantly expressed by genetic recombination and intracellularly produced, characterized in that the *Chiridius poppei*-derived fluorescent protein used therefor is a *Chiridius poppei*-derived wild-type fluorescent protein CpYGFP comprising the following amino acid sequence (SEQ ID NO: 1):

```
MTTFKIESRI HGNLNGEKFE LVGGGVGEEG RLEIEMKTKD KPLAFSPFLL SHCMGYGFYH    60

FASFPKGTKN IYLHAATNGG YTNTRKEIYE DGGILEVNFR YTYEFNKIIG DVECIGHGFP   120

SQSPIFKDTI VKSCPTVDLM LPMSGNIIAS SYARAFQLKD GSFYTAEVKN NIDFKNPIHE   180

SFSKSGPMFT HRRVEETHTK ENLAMVEYQQ VFNSAPRDM                         219
``` as its full-length amino acid sequence, or a *Chiridius poppei*-derived modified fluorescent protein CpYGFP H52F comprising the following amino acid sequence (SEQ ID NO: 3):

```
MTTFKIESRI HGNLNGEKFE LVGGGVGEEG RLEIEMKTKD KPLAFSPFLL SFCMGYGFYH   60

FASFPKGTKN IYLHAATNGG YTNTRKEIYE DGGILEVNFR YTYEFNKIIG DVECIGHGFP  120

SQSPIFKDTI VKSCPTVDLM LPMSGNIIAS SYARAFQLKD GSFYTAEVKN NIDFKNPIHE  180

SFSKSGPMFT HRRVEETHTK ENLAMVEYQQ VFNSAPRDM                        219
``` as its full-length amino acid sequence, a wild-type plant used in the process for generation of the aimed transformed plant capable of emitting fluorescence is a plant which is capable of undergoing *Agrobacterium* infection and producing a harvestable T1 seed through the self-pollination of each plant individual, and the process for generation of the aimed transformed plant capable of emitting fluorescence comprises the steps of:

inserting a DNA fragment encoding the full-length amino acid sequence of the *Chiridius poppei*-derived fluorescent protein into the cloning site of a T-DNA-based binary vector;

introducing the obtained T-DNA-based binary vector into a host bacterium of the genus *Agrobacterium* such that the bacterium of the genus *Agrobacterium* is transformed therewith;

infecting the wild-type plant with the obtained transformant of the bacterium of the genus *Agrobacterium* such that a T-DNA region contained in the T-DNA-based binary vector is recombinantly introduced in the chromosomal DNA of the wild-type plant to obtain a transformed plant;

subjecting each individual of the obtained transformed plant to self-pollination, and then harvesting a T1 seed from the plant individual; and sowing the obtained T1 seed and screening each grown plant to select a transformed plant individual to which a fluorescent phenotype attributed to the recombinant expression of the fluorescent protein in the leaf surface of the plant has been imparted.

Particularly, it is preferable that a garden plant which is capable of undergoing *Agrobacterium* infection and producing a harvestable T1 seed through the self-pollination of each plant individual is selected as the wild-type plant used in the process for generation of the aimed transformed plant capable of emitting fluorescence.

Effects of the Invention

In the present invention, in the process for generation of the transformed plant capable of emitting fluorescence, the DNA fragment encoding the full-length amino acid sequence of the *Chiridius poppei*-derived fluorescent protein is inserted into the T-DNA-based expression vector system, which is in turn introduced into the chromosomal DNA of a plant such that the *Chiridius poppei*-derived fluorescent protein is recombinantly expressed in the cell of the plant. The mature fluorescent protein thus produced therein is used as a fluorescence source of the plant. A peak wavelength $\lambda_{em}$ of the fluorescence spectrum of this *Chiridius poppei*-derived fluorescent protein as well as a peak wavelength $\lambda$ex. of the wavelength distribution of excitation light (excitation spectrum) that causes the fluorescence exists in the range of wavelength regions 600 nm to 490 nm. Therefore, the excitation of the fluorescent protein with light and fluorescence collection therefrom can be achieved using a "window" in the range of wavelengths 600 nm to 490 nm between two absorption bands of red and blue-violet regions, exhibited by chlorophyll a and chlorophyll b that are present in large amounts in the epidermal cell of the leaf.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 8a-b show a printed-out of image recorded by digital camera, wherein after primary screening based on the presence or absence of hygromycin resistance, the primarily selected individual is transplanted into soil and subjected to phenotypic screening based on the presence or absence of recombinantly expressed CpYGFP-derived fluorescence emitted from the surface of its true leaf on exposure to dark light (UV light source) at the stage when the true leaves have come out, and the individual (11-3-3.) thus secondarily selected as a fluorescent individual is observed at the time of blooming for (a) its overall appearance profile and (b) the presence or absence of recombinantly expressed CpYGFP-derived fluorescence from the whole plant on exposure to dark light (UV light source);

FIGS. 9a-b show a printed-out of image recorded by digital camera, wherein after primary screening based on the presence or absence of hygromycin resistance, the primarily selected individual is transplanted into soil and subjected to phenotypic screening based on the presence or absence of recombinantly expressed CpYGFP-derived fluorescence emitted from the surface of its true leaf on exposure to dark light (UV light source) at the stage when the true leaves have come out, and the individual (8-4) thus secondarily selected as a fluorescent individual is observed at the time of blooming for (a) its overall appearance profile and (b) the presence or absence of recombinantly expressed CpYGFP-derived fluorescence from the whole plant on exposure to dark light (UV light source);

FIG. 10 shows results, wherein amino acid sequences constituting corresponding secondary structures are aligned based on the comparison of the crystal structure of the *Chiridius poppei*-derived GFP-like fluorescent protein CpYGFP (SEQ ID NO: 1) determined by X-ray crystallographic analysis with the already reported crystal structures of DsRed (SEQ ID NO: 16) and aqGFP (SEQ ID NO: 17). The partial sequence of each secondary structure identified in the crystal structure of CpYGFP is additionally indicated under the sequences; and crystal structures of DsRed and aqGFP. The partial sequence of each secondary structure identified in the crystal structure of CpYGFP is additionally indicated under the sequences.

BEST MODE FOR CARRYING OUT THE INVENTION

Figure 1:
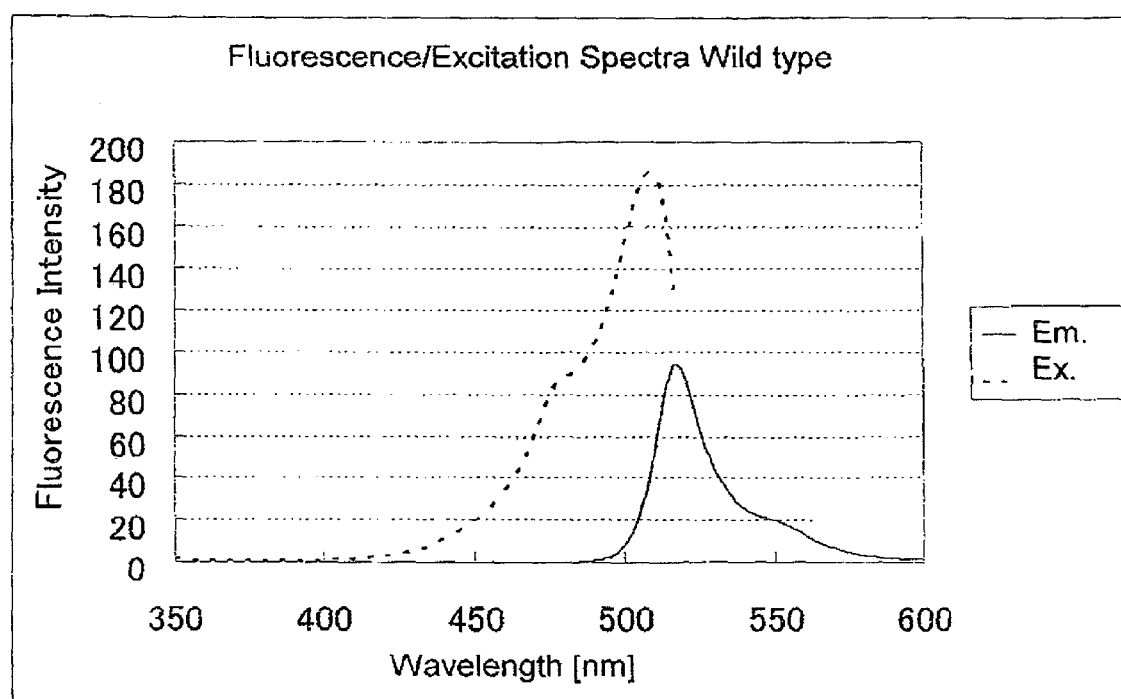
FIG. 1 is a chart showing the fluorescence and excitation spectra of the *Chiridius poppei*-derived GFP-like fluorescent protein CpYGFP.
Figure 2:
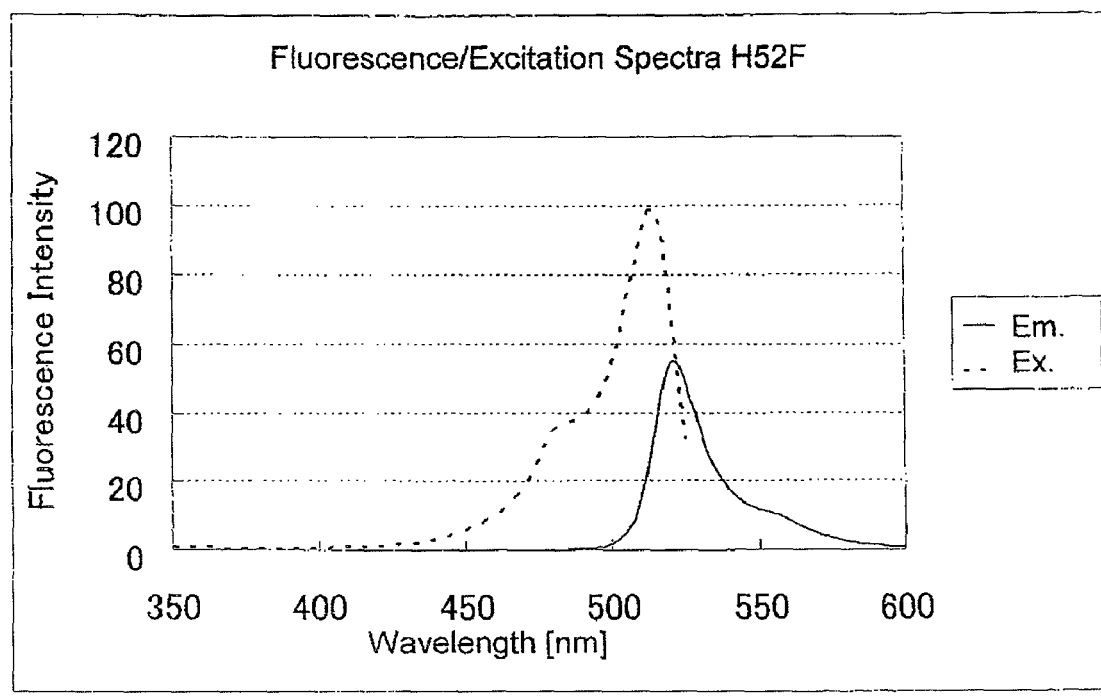
FIG. 2 is a chart showing the fluorescence and excitation spectra of the modified fluorescent protein CpYGFP H52F.

Hereinafter, the present invention will be further explained in detail

In the present invention, in the process for generation of a transformed plant capable of emitting fluorescence, a DNA fragment encoding the full-length amino acid sequence of a *Chiridius poppei*-derived fluorescent protein is inserted into a T-DNA-based expression vector system, which vector is in turn introduced into the chromosomal DNA of a plant such that the *Chiridius poppei*-derived fluorescent protein is recombinantly expressed in the cell of the plant. The mature fluorescent protein thus produced is used as a fluorescence source of the plant.

The T-DNA-based expression vector system, which is used as means for introducing the DNA fragment encoding the full-length amino acid sequence of the *Chiridius poppei*-derived fluorescent protein into the chromosomal DNA of a plant, is a recombinant expression system that has been employed in the development of the Fox-hunting system (full-length cDNA over-expression gene hunting system) disclosed in WO 03/018808 A1. Specifically, a foreign promoter, polyadenylation signal sequence, and terminator are placed in a region flanked by the two T-DNA border nucleotide sequences on the upward and downward sides in the *E. coli/Agrobacterium* binary vector. The DNA fragment of interest is inserted to a site between the promoter and the polyadenylation signal sequence. This *E. coli/Agrobacterium*. binary vector comprising the insert of the DNA fragment of interest is introduced into *Agrobacterium tumefaciens* having a Ti-plasmid to prepare a transformant. Then, a target plant is infected with this transformant to generate a transformed plant.

Using this transformation method, the introduction of the region flanked by two T-DNA border nucleotide sequences, which is contained in the binary vector, into the chromosomal DNA of the target plant is promoted by products expressed from the genes of gene clusters VirA, VirB, VirC, VirD, VirE, and VirG, which are present in the Vir region contained in the *Agrobacterium tumefaciens* Ti-plasmid. Specifically, the region flanked by the two T-DNA border nucleotide sequences, which is included in the binary vector, is introduced into the same site to which the original T-DNA of the *Agrobacterium tumefaciens* will be inserted by *Agrobacterium tumefaciens* infection, In actual, the *Agrobacterium tumefaciens* transformant also retains its original T-DNA region. Thus, in addition to the transformed plants in which the region flanked by the two T-DNA border nucleotide sequences in the binary vector is introduced, some of transformed plants in which the original T-DNA region is introduced are also generated. However, transformed plants can be screened by confirming whether or not tumor (crown gall) is caused in the plant, to eliminate those having the introduced original T-DNA is region.

In particular, cloning site that is placed in an *E. coli*/Agro-bacterium binary vector pBIG2113SF, specifically, that composed of two SfiI restriction sites, is used to insert the DNA fragment of interest into the binary vector in advance. In the case of the cloning site composed of the two SfiI restriction sites, the corresponding SfiI restriction sites are equipped at upward and downward of the DNA fragment of interest in advance, so that the DNA fragment of interest can be inserted selectively downward of the promoter sequence in a sense direction.

The introduction of the region flanked by the two T-DNA border nucleotide sequences in the binary vector into the chromosomal DNA of the plant via the *Agrobacterium tumefaciens* transformant is usually introduction into one site per plant. Specifically, diploid chromosomal DNA contains a chromosome a* that has undergone the homologous replacement-based genetic recombination of the T-DNA region comprising the insert of the foreign gene and a homologous chromosome a that has not undergone the genetic recombination, and takes (a*/a)-type chromosome constitution. Thus, each individual of the obtained transformed plant (a*/a) is subjected to self-pollination, and then a T1 seed is harvested from the plant individual. The obtained T1 seed takes any of four chromosome constitutions (a*/a*), (a*/a), (a/a*), and (a/a). A drug resistance gene is incorporated in advance into the T-DNA region comprising the insert of the foreign gene. As a result, the obtained T1 seed can be screened based on whether or not it has the drug resistance to select those having the (a*/a*)-, (a*/a)-, or (a/a*)-type chromosome constitution.

In addition, the introduction of the T-DNA region comprising the insert of the foreign gene into the chromosomal DNA of the plant via the *Agrobacterium tumefaciens* transformant takes place with exceedingly high frequency in particular chromosomal DNA among plurality of chromosomal DNAs carried by the plant. As a result, such introduction almost never takes place in two or more sites per plant. On the other hand, in the transformed plant generated by the transformation procedure used in the present invention, such introduction never takes place in two or more sites per plant by properly selecting a bacterial cell density in a suspension of the *Agrobacterium tumefaciens* transformant used for infection by a floral dipping method. Moreover, the intended drug used for selection based on the drug resistance gene is added at an appropriate concentration in a medium at the stage of germination of the obtained T1 seed, and thereby, those having the (a*/a*)-, (a*/a)-, or (a/a*)-type chromosome constitution can be selected in the screening.

Any drug resistance gene which is capable of being expressed at a proper expression level in the cell of the target plant may be used as the drug resistance gene that is incorporated in advance in the region flanked by two T-DNA border nucleotide sequences in the binary vector and used in this screening based on the drug resistance gene. Particularly, it is preferable that the drug resistance gene is capable of being expressed at a proper expression level in T1 seed germination. For example, a hygromycin resistance gene can be used preferably.

After primary screening based on the presence or absence of expression of the drug resistance gene, the selected plant having the (a*/a*)-, (a*/a)-, or (a/a*)-type chromosome constitution is further cultivated. Whether or not the *Chiridius poppei*-derived fluorescent protein is actually expressed as a mature protein from the incorporated DNA fragment in the epidermal cell of the grown plant leaf is confirmed.

In the present invention, the aimed gene encoding the *Chiridius poppei*-derived fluorescent protein is expressed in the epidermal cell of the leaf, in which cell a large amount of intracellular chlorophyll is present. In such a case, the gene encoding the *Chiridius poppei*-derived fluorescent protein is transcribed to mRNA using a foreign promoter that is capable of achieving a proper transcription level in the epidermal cell of the plant leaf. According to the object of the present invention, a foreign promoter is used, which is capable of achieving a proper transcription level in the epidermal cell of the leaf of the target plant, when cultivated under the same growth conditions as those used for a wild-type species of the plant. A promoter for homeostatic expression capable of functioning in the epidermal cell of the plant leaf is suitable as the foreign promoter that satisfies this requirement. Examples of the promoter for constitutive expression that can be used preferably include a cauliflower mosaic virus 35S promoter sequence. The promoter for constitutive expression constitutively induces expression. Moreover, expression frequency thereof does not show a large variation. Therefore, a substantially uniform expression level can be achieved in the epidermal cell of the grown plant leaf.

As described later, the *Chiridius poppei*-derived fluorescent protein is folded as a protein having a predetermined three-dimensional structure post to transcription/translation, in similar manner to the fluorescent proteins derived from other species. Furthermore, this protein functions as a fluorescent protein, only when its fluorophore is formed inside thereof. Specifically, only when, post to the transcription/translation, the protein folding into its three-dimensional structure as well as the formation of its aimed fluorophore inside thereof is completed, its original fluorescent properties, particularly, a peak wavelength of fluorescence and an absorption maximum wavelength, are obtained. The major advantage of the present invention is in that the *Chiridius poppei*-derived fluorescent protein indeed achieves the aimed fluorophore formation, as described later, with high efficiency in the epidermal cell of the plant leaf. Specifically, the advantage of the present invention is in that the *Chiridius poppei*-derived fluorescent protein used in the present invention achieves the protein folding into its predetermined three-dimensional structure as well as the aimed fluorophore formation with high efficiency, although the inside of the epidermal cell of the plant leaf differs in environment from the inside of a microorganism or animal cell. Particularly, in the case of the *Chiridius poppei*-derived fluorescent protein used in the present invention, its fluorophore with a p-hydroxybenzylideneimidazolinone structure is formed through the cyclization of its "GYG" portion and subsequent oxidization. In this case, it is further required that the imidazole ring of a side chain of a His residue or the benzene ring of a Phe residue should have arrangement capable of "π-π stacking" relative to a π-conjugated system which the fluorophore has. The advantage of the present invention is in that the aimed fluorophore formation including this arrangement is achieved with high efficiency even in the inside of the epidermal cell of the plant leaf.

The formation of its original fluorophore including the "π-π stacking" is achieved even in the inside of the epidermal cell of the plant leaf. As a result, a peak wavelength $\lambda_{em.}$ of the fluorescence spectrum of this fluorescent protein as well as a peak wavelength $\lambda_{ex.}$ of the wavelength distribution of excitation light (excitation spectrum) that causes the fluorescence exists in the range of wavelength regions 600 nm to 490 nm. Therefore, the excitation of the fluorescent protein with light and fluorescence collection therefrom can be achieved using a "window" in the range of wavelengths 600 nm to 490 nm between two absorption bands of red and blue-violet regions, exhibited by chlorophyll a and chlorophyll b present in large amounts in the epidermal cell of the leaf.

The cDNA fragment encoding the full-length amino acid sequence of the *Chiridius poppei*-derived fluorescent protein CpYGFP (*Chiridius poppei* Yellowish Green Fluorescent Protein), which is used in the present invention, has been inserted to the cloning site, between Blunt-XhoI sites, of a cloning vector pBluescript II SK to construct a plasmid pBluescriptII SK-NFP. The pBluescriptII SK-NFP has been internationally deposited (on Mar. 31, 2004) as deposition No. FERM BP-08681 with International Patent Organism Depositary, National Institute of Advanced Industrial Science and Technology (Tsukuba Central 6, 1-1 Higashi, Tsukuba, Ibaraki, 305-8566, Japan) under the Budapest Treaty.

The cDNA fragment encoding the full-length amino acid sequence of the wild-type CpYGFP, which is inserted in the pBluescriptII SK-NFP, has been identified as a nucleotide sequence of 782 by in full length with ORF (translation frame) of 660 bp. The whole nucleotide sequence thereof and an amino acid sequence of 219 amino acids in length deduced from the ORF are shown as follows:

```
                                                        (SEQ ID NO: 5)
AGAACACTCA GTGTATCCAG TTTTCCGTCC TACTACAAAC              40

ATG ACA ACC TTC AAA ATC GAG TCC CGG ATC CAT GGC AAC CTC AAC GGG    88
 M   T   T   F   K   I   E   S   R   I   H   G   N   L   N   G
 1               5                  10                  15

GAG AAG TTC GAG TTG GTT GGA GGT GGA GTA GGT GAG GAG GGT CGC CTC    136
 E   K   F   E   L   V   G   G   G   V   G   E   E   G   R   L
                20                  25                  30

GAG ATT GAG ATG AAG ACT AAA GAT AAA CCA CTG GCA TTC TCT CCC TTC    184
 E   I   E   M   K   T   K   D   K   P   L   A   F   S   P   F
                35                  40                  45

CTG CTG TCC CAC TGC ATG GGT TAC GGG TTC TAC CAC TTC GCC AGC TTC    232
 L   L   S   H   C   M   G   Y   G   F   Y   H   F   A   S   F
            50                  55                  60

CCA AAG GGG ACT AAG AAC ATC TAT CTT CAT GCT GCA ACA AAC GGA GGT    280
 P   K   G   T   K   N   I   Y   L   H   A   A   T   N   G   G
 65                  70                  75                  80

TAC ACC AAC ACC AGG AAG GAG ATC TAT GAA GAC GGC GGC ATC TTG GAG    328
 Y   T   N   T   R   K   E   I   Y   E   D   G   G   I   L   E
                    85                  90                  95

GTC AAC TTC CGT TAC ACT TAC GAG TTC AAC AAG ATC ATC GGT GAC GTC    386
 V   N   F   R   Y   T   Y   E   F   N   K   I   I   G   D   V
                100                 105                 110

GAG TGC ATT GGA CAT GGA TTC CCA AGT CAG AGT CCG ATC TTC AAG GAC    424
 E   C   I   G   H   G   F   P   S   Q   S   P   I   F   K   D
            115                 120                 125

ACG ATC GTG AAG TCG TGT CCC ACG GTG GAC CTG ATG TTG CCG ATG TCC    472
 T   I   V   K   S   C   P   T   V   D   L   M   L   P   M   S
        130                 135                 140

GGG AAC ATC ATC GCC AGC TCC TAC GCT AGA GCC TTC CAA CTG AAG GAC    520
 G   N   I   I   A   S   S   Y   A   R   A   F   Q   L   K   D
145                 150                 155                 160

GGC TCT TTC TAC ACG GCA GAA GTC AAG AAC AAC ATA GAC TTC AAG AAT    568
 G   S   F   Y   T   A   E   V   K   N   N   I   D   F   K   N
                165                 170                 175

CCA ATC CAC GAG TCC TTC TCG AAG TCG GGG CCC ATG TTC ACC CAC AGA    616
 P   I   H   E   S   F   S   K   S   G   P   M   F   T   H   R
                    180                 185                 190

CGT GTC GAG GAG ACT CAC ACC AAG GAG AAC CTT GCC ATG GTG GAG TAC    664
 R   V   E   E   T   H   T   K   E   N   L   A   M   V   E   Y
            195                 200                 205

CAG CAG GTT TTC AAC AGC GCC CCA AGA GAC ATG TAG                    700
 Q   Q   V   F   N   S   A   P   R   D   M   *
 210                 215

AATGTGGAAC GAAACCTTTT TTTCTGATTA CTTTCTCTGT TGACTCCACA             750

TTCGGAACTT GTATAAATAA GTTCAGTTTA AA                                782
```

The fluorescent properties exhibited by the *Chiridius poppei*-derived fluorescent protein CpYGFP and a cloning method for the cDNA encoding the fluorescent protein have already been published in Patent Documents (see WO 2005/095599 A1 and U.S. 2005/0221338 A1).

In addition, the structural specificity of the fluorophore that exhibits the feature of the fluorescent properties shown by this *Chiridius poppei*-derived fluorescent protein CpYGFP, that is, a peak wavelength 517 nm of fluorescence and a peak wavelength 509 nm in excitation spectrum, has been elucidated by the research group of the present applicant. Specifically, as a result of studying in detail a crystal structure shown in FIG. 3, particularly, a partial structure in which the fluorophore is focalized shown in FIG. 4, by X-ray crystallographic analysis of the recombinantly expressed CpYGFP, it has been confirmed that the fluorophore has a p-hydroxybenzylidene-imidazolinone structure formed through "GYG" cyclization and dehydration steps. Moreover, it has been shown that a main factor for determining the peak wavelength of fluorescence is that the imidazole ring on the side chain of His[52] has such arrangement capable of "π-π stacking" relative to a p-hydroxyphenyl group (phenol ring) derived from Tyr[56], which is contained in the fluorophore with a p-hydroxybenzylideneimidazolinone structure.

Figure 3:
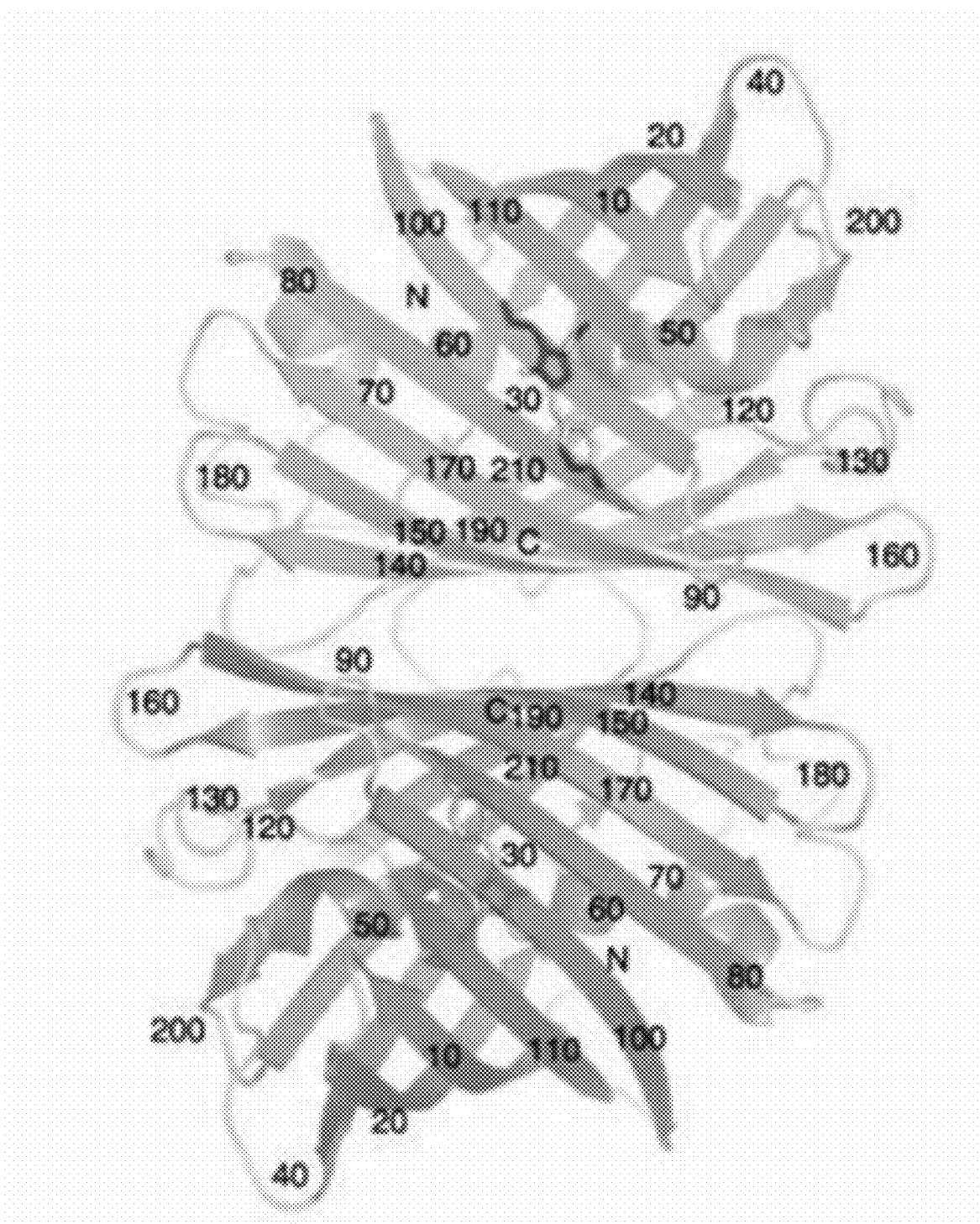
FIG. 3 is a drawing showing the crystal structure of the *Chiridius poppei*-derived GFP-like fluorescent protein CpYGFP, which is illustrated in the form of a stereo view, wherein the overall structure of CpYGFP present as a dimer in the unit cell of the crystal is indicated by means of a ribbon model.

Detailed data on coordinates of the fluorophore of the recombinantly expressed CpYGFP, that is, the crystal structure shown in FIG. 3, has been registered as ID code: 2DD7 in Protein Data Bank. Not only the overview shown in FIG. 3 but also the partial structure shown in FIG. 4 can be referred more specifically to three-dimensional graphics based on the data on coordinates.

In fact, in the determined three-dimensional structure of CpYGFP, eleven β-strands, an α-helix ($α_1$-helix) including GYG, which is involved in fluorophore construction, and another short α-helix ($α_2$-helix) constitute, as shown in FIG. 3, an overall form which is commonly shown in *A. victoria*-derived GFP and *Discosoma striata*-derived DsRFP, that is, a barrel structure called "β can". FIG. 10 shows, by the comparison of the amino acid sequence of CpYGFP with the amino acid sequences of *A. victoria*-derived GFP and *Discosoma striata*-derived DsRFP, that their secondary structure portions have commonality as a whole. Moreover, the GYG included in the α-helix that is located inside of the barrel actually forms the fluorophore with a p-hydroxybenzylidene-imidazolinone structure, as shown below, through cyclization and subsequent oxidization.

The mechanism under which CpYGFP is converted to a mature fluorescent protein post to translation, that is, the formation of the fluorophore with a p-hydroxybenzylidene-imidazolin-one structure from "GYG" present in the α-helix, is presumed to be attributed to the following process:

Step of folding post to translation; (arrangement into distorted configuration)

[Chemical Formula 1]

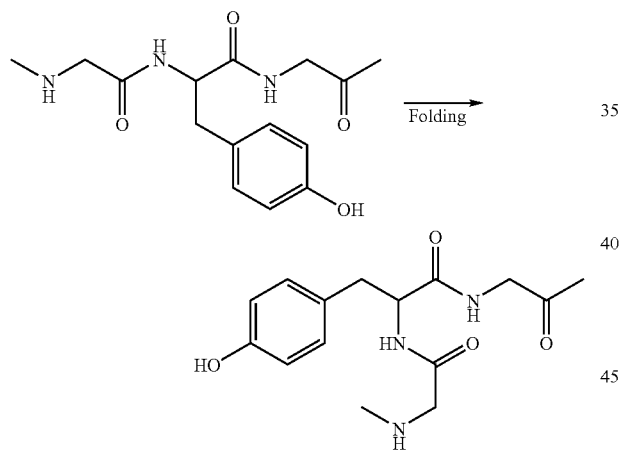

Cyclization and dehydration steps

[Chemical Formula 2]

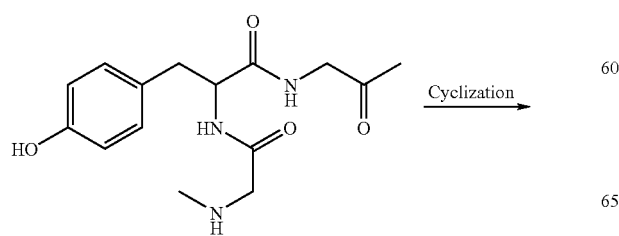

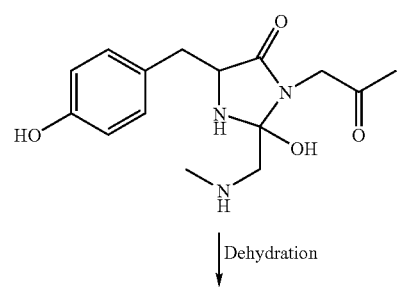

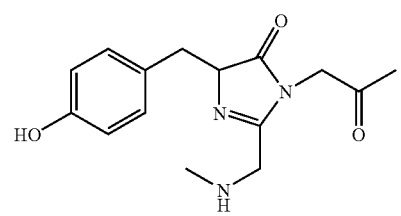

Oxidization step: completion of p-hydroxybenzylidene-imidazolinone structure

[Chemical Formula 3]

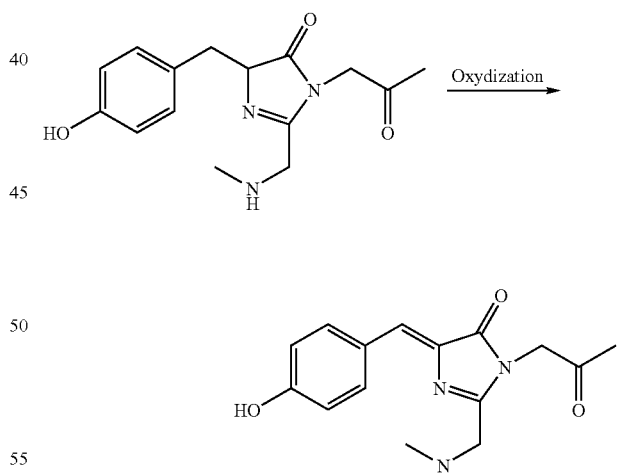

Finally, the fluorophore with a p-hydroxybenzylideneimidazolinone structure is kept in equilibrium between the following non-ionized and ionized forms:

Equilibrium between ionized and non-ionized forms in p-hydroxybenzylideneimidazolinone structure

[Chemical Formula 4]

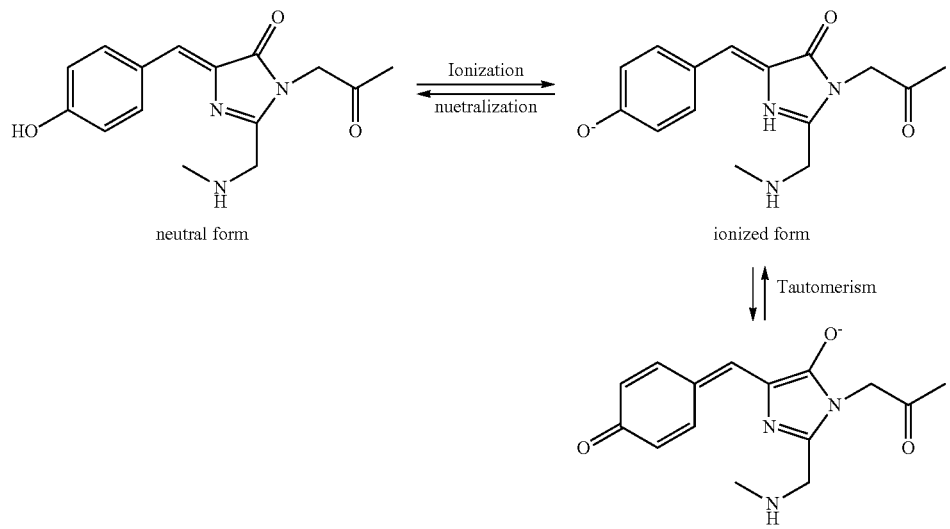

Figure 4:
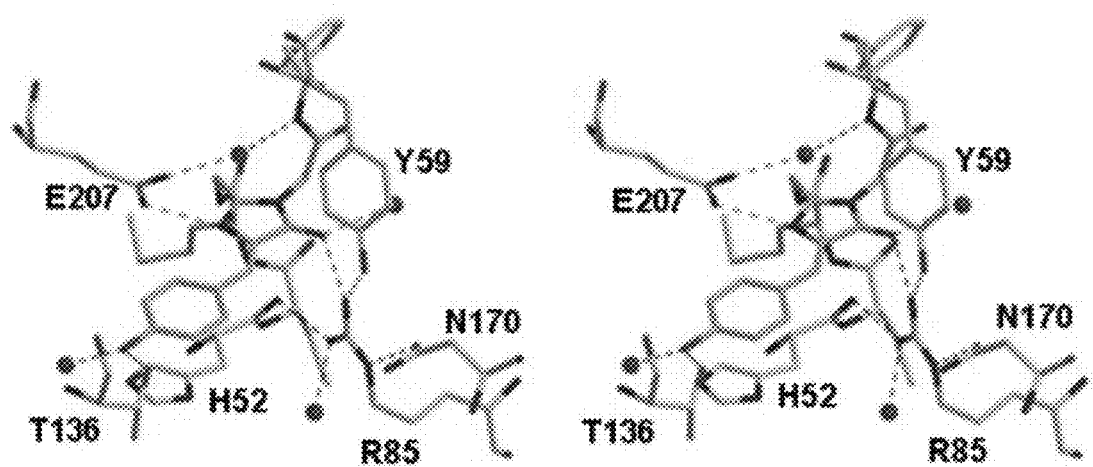
FIG. 4 is a drawing showing a partial structure, in which presented are a fluorophore with a p-hydroxybenzylideneimidazolinone structure formed from "GYG" in the *Chiridius poppei*-derived GFP-like fluorescent protein CpYGFP; the side-chain configuration of amino acid residues $His^{52}$, $Tyr^{59}$, $Arg^{85}$, $Thr^{136}$, $Asn^{170}$, and $Glu^{207}$ located in proximity thereto; and predicted hydrogen bonding and the location of the oxygen atom of a water molecule immobilized via the hydrogen bonding.

It has been revealed that local steric configuration including amino acid residues present in proximity to this fluorophore is as shown in FIG. 4. It is expected that in the wild-type CpYGFP as well, the form involved in its fluorescence is the ionized form, and Thr$^{136}$ present in the β-strand (β$_6$) makes some contribution to the stabilization of this ionized form. In addition, it is expected that in the wild-type CpYGFP, the imidazole ring of the side chain of His$^{52}$ is located overlapping with the Tyr-derived p-hydroxyphenyl group (phenol ring) portion in the fluorophore with the p-hydroxybenzylideneimidazolinone structure, and the interaction via the π-π overlap between them (π-π stacking) functions to cause the red shift of the fluorescence wavelength.

Moreover, in the present invention, fluorescent properties exhibited by the modified fluorescent protein CpYGFP H52F, which is used in the similar manner to the wild-type CpYGFP, are a peak wavelength 521.8 nm of fluorescence and a peak wavelength 513.6 nm in excitation spectrum.

Using the structural characteristic of the fluorophore that the wild-type CpYGFP has shown in FIG. 4, the His$^{52}$-derived imidazole ring is replaced by benzene ring derived from an aromatic amino acid Phe, which is capable of taking the corresponding configuration such that the interaction between the π-conjugated systems due to "π-π stacking" is. Increased to reduce excitation energy for the fluorescent state. As a result, the maximum wavelength (peak wavelength) of fluorescence of the modified fluorescent protein CpYGFP H52F is shifted to a wavelength longer than that of the wild-type CpYGFP (red-shifted).

On the other hand, a gene encoding the full-length amino acid sequence of the modified fluorescent protein CpYGFP H52F can be prepared, for example, using site-specific mutagenesis according to the following procedure.

The gene encoding the H52F modified protein is prepared by site-specific mutagenesis using, as a template, a wild-type CpYGFP-encoding gene inserted in a recombinant expression vector pET101-NFP for *Chiridius poppei*-derived CpYGFP disclosed in WO 2005/095599 A1.

To substitute a codon CAC encoding His$^{52}$ by a codon TTC encoding Phe, a DNA fragment is prepared by a PCR method using primers shown below. Specifically, a primer shown below in which the codon substitution has been introduced at the 5' end is used as a forward primer for the PCR. On the other hand, a primer having a nucleotide sequence complementary to the partial nucleotide sequence (nucleotides Nos. 125 to 153; partial sequence shown below) upward of the codon CAC encoding His$^{52}$ is used as a reverse primer.

```
                                           (SEQ ID NO: 12)
 5'-A CTG GCA TTC TCT CCC TTC CTG CTG TCC-3'

(SEQ ID NO: 13)
 3'-T GAC CGT AAG AGA GGG AAG GAC GAC AGG-5'

(SEQ ID NO: 14)
   Leu Ala Phe Ser Pro Phe Leu Leu Ser
        45                  50
```

Specifically, used as a forward primer for PCR for the point mutation of H52F is the following CpYGFP/H52F UP (30 mer):

```
                                           (SEQ ID NO: 6)
 5'-TTC TGC ATG GGT TAC GGG TTC TAC CAC TTC-3'
```

On the other hand, used as a common reverse primer is a reverse primer CpYGFP/LP153 (28 mer):

```
                                           (SEQ ID NO: 7)
 5'-GGA CAG CAG GAA GGG AGA GAA TGC CAG T-3'
```

The recombinant expression vector pET101-NFP for CpYGFP is used as a template under conditions shown below to prepare a PCR amplification product of approximately 6.4 kbp corresponding to the full length of the plasmid. Temperature conditions for the PCR reaction used are shown in Table 1, and the composition of a reaction solution used is shown in Table 2. A sufficiently long time is selected as an extension time in consideration of a nucleotide length to be extended as long as approximately 6.4 kbp.

TABLE 1-1

Temperature conditions for PCR reaction:
Apparatus used: Mastercycler Gradient (Eppendorf)

| Cycle operation | Temperature (° C.) | Time | |
|---|---|---|---|
| denature | 96 | 1 min | |
| anneal | 60 | 5 sec | |
| extention | 68 | 6 min 30 sec | 15 times |
| denature | 96 | 5 sec | |
| extention | 68 | 6 min 30 sec | |
| store | 10 | overnight (14 hrs) | |

TABLE 1-2

Composition of reaction solution

| Component | Concentration of stock solution | Mixed amount (μL) | Final Concentration |
|---|---|---|---|
| H$_2$O | | 48.75 | |
| Pyro Buffer | 10 x | 7.5 | 1 x |
| dNTP | 2 mM | 7.5 | 0.2 mM |
| Pyrobest DNA Pol. | 5 u/μL | 0.75 | 0.05 u/μL |
| Forward primer | 10 μM | 1.5 | 0.2 μM |
| CpYGFP/ LP153 | 10 μM | 1.5 | 0.2 μM |
| Template plasmid | 1 μg/μL | 7.5 | 1 ng/μL |
| Total | | 75.0 | |

The prepared PCR amplification product is purified according to procedures below.

After PCR reaction is carried out using 25 μL each of a reaction solution, three reaction solutions in total are gathered, and a 5 μL aliquot of the reaction solution is collected and electrophoresed on a 0.7% agarose gel to confirm the aimed PCR amplification product having the molecular weight of approximately 6.4 kbp.

Subsequently, the product DNA is concentrated from the reaction solution using MinElute PCR Purification Kit (manufactured by QIAGEN). 5 volumes (350 μL) of a PB buffer per volume (70 μL) of the reaction solution are added thereto, and the mixture is vortexed and then transferred to a MinElute column. After centrifugation for 30 seconds, the precipitated DNA is separated as a pellet, and the supernatant is removed. The precipitated DNA is washed with 0.7 mL of a PE buffer and centrifuged (15,000 rpm) for 1 minute. Furthermore, 20 μL of an EB buffer is added thereto, and the mixture is left at rest at room temperature for 1 minute. Then, the mixture is centrifuged (15,000 rpm) for 1 minute, and the supernatant is collected.

To the collected DNA solution, 3 μL of 10×buffer (500 mM Tris/HCl pH 9.5, 100 μM MgCl$_2$, 50 mM DTT), 3 μL of 50% glycerol, and 3 mL of 75 mM ATP are added, and the mixture is vortexed. Then, 1 μL of T4 PNK (Polynucleotide kinase) is added thereto, and the mixture is incubated at 37° C. for approximately 30 minutes.

After addition of 3 μL of 10×loading dye solution, 33 μL of the DNA solution per lane is electrophoresed on a 0.7% TAE agarose gel. The aimed band of approximately 6.4 kbp is excised from the gel. The excised gel slice is centrifuged (7000 rpm) for 10 minutes using Ultrafree-DA (purchased from MILLIPORE) to extract the DNA solution into a 1.5-mL Eppendort tube from the gel slice. The DNA product is concentrated from the extract using MinElute PCR Purification Kit (purchased from QIAGEN). 5 volumes of the PB buffer per volume of the reaction solution are added thereto, and the mixture is vortexed and then transferred to a MinElute column. After centrifugation for 30 seconds, the precipitated DNA is separated as a pellet, and the supernatant is removed. The precipitated DNA is washed with 0.7 mL of the PE buffer and centrifuged (15,000 rpm) for 1 minute. Furthermore, 10 μL of the EB buffer is added thereto, and the mixture is left at rest at room temperature for 1 minute. Then, the mixture is centrifuged (15,000 rpm) for 1 minute, and the supernatant is collected. The collected supernatant is used as a solution of purified double-stranded DNA.

A 1 μL aliquot of the solution of purified double-stranded DNA is mixed with 1 μL of Ligation high (purchased from Toyobo), and the mixture is subjected to ligation reaction overnight at 16° C. By this ligation reaction, the double-stranded DNA is ligated at both ends to construct a circular plasmid. Each plasmid have the same construction as that of the template recombinant expression vector pET101-NFP for CpYGFP except for the introduced point mutation, and serves as a recombinant expression vector for the modified protein.

After ligation, a TOP10 cell is transformed with the whole amount (2 μL) of the ligation solution and inoculated onto an LB plate containing carbenicillin. The next morning, several colonies that retain the resistance gene for the drug present in the plasmid vector are collected. The collected colonies are inoculated on an LB medium containing carbenicillin such that the transformed E. coli is proliferated to multiply the plasmid vector. The collected transformed E. coli is subjected to lysis to collect DNA therefrom, and then the aimed circular DNA molecule (plasmid vector) having the molecular weight of approximately 6.4 kbp is isolated and purified.

To certify the nucleotide sequence of the gene encoding the modified protein, which is contained in each purified plasmid vector, the DNA fragment is amplified by PCR using, as a template, the region encording the modified protein, which is contained in the plasmid vector, and then a sample for sequencing is prepared therefrom.

In the step, an amplification product of 673 by in nucleotide length is prepared using the following primers for PCR, which were disclosed in WO 2005/095599 A1:

A forward primer pET-UP1 (28 mer):

```
                                       (SEQ ID NO: 8)
     5'-CACCATGACAACCTTCAAAATCGAGTCC-3'
```

A reverse primer SalI-LP1 (35 mer):

```
                                       (SEQ ID NO: 9)
     5'-CTCGTCGACCTACATGTCTCTTGGGGCGCTGTTGA-3'
```

The sample for sequencing prepared from the DNA fragment of 673 bp is applied to, for example, a commercially available sequencer ABI PRISM 310 Genetic Analyzer to respectively conduct sequencing from the 5' end and sequencing from the 3' end.

The results of sequencing from the 5' end and sequencing from the 3' end are integrated to confirm that the aimed site-specific mutation is introduced in the nucleotide sequence of the region encoding the modified protein, and that the sequence is free from errors that occur during PCR amplification.

According to the site-specific mutagenesis, a DNA fragment having a nucleotide sequence of 782 by in full length with ORF (translation frame) of 660 by contained therein can be prepared as the cDNA fragment encoding the full-length amino acid sequence of the modified fluorescent protein CpYGFP H52F. The whole nucleotide sequence that has undergone the site-specific mutagenesis and an amino acid sequence of 219 amino acids in length deduced from the ORF thereof are shown as follows:

```
                                                           (SEQ ID NO: 15)
AGAACACTCA GTGTATCCAG TTTTCCGTCC TACTACAAAC                       40

ATG ACA ACC TTC AAA ATC GAG TCC CGG ATC CAT GGC AAC CTC AAC GGG   88
 M   T   T   F   K   I   E   S   R   I   H   G   N   L   N   G
 1               5                  10                  15

GAG AAG TTC GAG TTG GTT GGA GGT GGA GTA GGT GAG GAG GGT CGC CTC  136
 E   K   F   E   L   V   G   G   G   V   G   E   E   G   R   L
                 20                  25                  30

GAG ATT GAG ATG AAG ACT AAA GAT AAA CCA CTG GCA TTC TCT CCC TTC  184
 E   I   E   M   K   T   K   D   K   P   L   A   F   S   P   F
             35                  40                  45

CTG CTG TCC TTC TGC ATG GGT TAC GGG TTC TAC CAC TTC GCC AGC TTC  232
 L   L   S   F   C   M   G   Y   G   F   Y   H   F   A   S   F
         50                  55                  60

CCA AAG GGG ACT AAG AAC ATC TAT CTT CAT GCT GCA ACA AAC GGA GGT  280
 P   K   G   T   K   N   I   Y   L   H   A   A   T   N   G   G
65                  70                  75                  80

TAC ACC AAC ACC AGG AAG GAG ATC TAT GAA GAC GGC GGC ATC TTG GAG  328
 Y   T   N   T   R   K   E   I   Y   E   D   G   G   I   L   E
                     85                  90                  95

GTC AAC TTC CGT TAC ACT TAC GAG TTC AAC AAG ATC ATC GGT GAC GTC  386
 V   N   F   R   Y   T   Y   E   F   N   K   I   I   G   D   V
                 100                 105                 110

GAG TGC ATT GGA CAT GGA TTC CCA AGT CAG AGT CCG ATC TTC AAG GAC  424
 E   C   I   G   H   G   F   P   S   Q   S   P   I   F   K   D
             115                 120                 125

ACG ATC GTG AAG TCG TGT CCC ACG GTG GAC CTG ATG TTG CCG ATG TCC  472
 T   I   V   K   S   C   P   T   V   D   L   M   L   P   M   S
         130                 135                 140

GGG AAC ATC ATC GCC AGC TCC TAC GCT AGA GCC TTC CAA CTG AAG GAC  520
 G   N   I   I   A   S   S   Y   A   R   A   F   Q   L   K   D
145                 150                 155                 160

GGC TCT TTC TAC ACG GCA GAA GTC AAG AAC AAC ATA GAC TTC AAG AAT  568
 G   S   F   Y   T   A   E   V   K   N   N   I   D   F   K   N
                     165                 170                 175

CCA ATC CAC GAG TCC TTC TCG AAG TCG GGG CCC ATG TTC ACC CAC AGA  616
 P   I   H   E   S   F   S   K   S   G   P   M   F   T   H   R
                 180                 185                 190

CGT GTC GAG GAG ACT CAC ACC AAG GAG AAC CTT GCC ATG GTG GAG TAC  664
 R   V   E   E   T   H   T   K   E   N   L   A   M   V   E   Y
             195                 200                 205

CAG CAG GTT TTC AAC AGC GCC CCA AGA GAC ATG TAG                  700
 Q   Q   V   F   N   S   A   P   R   D   M   *
         210                 215

AATGTGGAAC GAAACCTTTT TTTCTGATTA CTTTCTCTGT TGACTCCACA           750

TTCGGAACTT GTATAAATAA GTTCAGTTTA AA                              782
```

The wild-type plant used in the process for generation of the aimed transformed plant capable of emitting fluorescence according to the approach of the present invention is a plant which is capable of undergoing *Agrobacterium* infection and producing a harvestable T1 seed through the self-pollination of each plant individual. The approach has very significant effects in such a case where a large amount of intracellular chlorophyll is present in the cell, inparticular, in the epidermal cell of its leaf. The infectivity of a bacterium of the genus *Agrobacterium* is utilized in the step of transformation of the plant. Therefore, the present invention can be applied to any of a dicotyledon and a monocotyledon, which undergo *Agrobacterium* infection. It is preferable that any plant belonging to the family Brassicaceae, Poaceae, Solanaceae, or Leguminosae is selected as the wild-type plant used in the process for generation of the aimed transformed plant capable of emitting fluorescence.

For example, any of the following plants may be selected as the wild-type plant used in the process for generation of the aimed transformed plant capable of emitting fluorescence:
the family Brassicaceae: *Arabidopsis thaliana*,
the family Solanaceae. *Nicotiana tabacum*, the family Poaceae: *Zea mays, Oryza sativa*, and
the family Leguminosae: *Glycine max*

Furthermore, among variety of garden plants, the following plants:
a rose: the family Rosaceae, the genus *Rosa;*
*Dianthus caryophyllus*: the family Caryophyllaceae, the genus *Dianthus;*
a chrysanthemum, particularly, a cultivated chrysanthemum (*Chrysanthemum morifolium*): the family Compositae, the genus *Chrysanthemum;*
*Gerbera* cvs.: the family Compositae, the genus *Gerbera;*
*Eustoma grandiflorum*: the family Gentianaceae, the genus *Eustoma;*
*Petuniaxhybrida*: the family Solanaceae, the genus *Petunia;*
*Torenia fournieri*: the family Scrophulariaceae, the genus *Torenia;*
*Nierembergia hippomanica*: the family Solanaceae, the genus *Nierembergia;*
garden verbena: the family Verbenaceae, the genus *Verbena;*
*Calibrachoa* hybrid Cultivar: the family Solanaceae, the genus *Calibrachoa;*
*Cyclamen persicum*: the family Primulaceae, the genus *Cyclamen*; Cactaceae, for example,
the family Cactaceae, the genera *Austrocylindropuntia, Astrophytum, Echinocactus, Echinocereus, Echinopsis, Epiphyllum, Opuntia, Schlumbergera, Chamaecereus, Cylindropuntia, Gymnocalycium, Zygocactus, Selenicereus, Tephrocactus, Neobuxbaumia, Neoraimondia, Nopalea, Ferocactus, Mammillaria, Melocactus, Rhipsalis, Roseocactus,* and *Lophosphora*; and
an orchid, for example,
*Phalaenopsis* cvs.: the family Orchidaceae, the genus *Phalaenopsis;*
*Cymbidium* cvs.: the family Orchidaceae, the genus *Cymbidium;*
*Dendrobium nobile* hybrids, *D. phalaenopsis* hybrids: the family Orchidaceae, the genus *Dendrobium;*
*Oncidium* cvs.: the family Orchidaceae, the genus *Oncidium*; and
*Cattleya* cvs.: the family Orchidaceae, the genus *Cattleya* can be exemplified as the plant which is capable of undergoing infection with the transformed bacterium obtained by introducing the T-DNA-based binary vector into a host bacterium of the genus *Agrobacterium*, and generating a transformed plant. In the case when the present invention is applied to a garden plant, any of these plants may be selected as the wild-type plant used in the process for generation of the aimed transformed plant capable of emitting fluorescence.

In the present invention, in the transformed plant, the aimed DNA fragment encoding the full-length amino acid sequence of the fluorescent protein is incorporated in the chromosomal DNA thereof. The transformed plant is screened by germinating a T1 seed thereof. Thus, for the plant, it is preferable that a cell in its meristem differentiated into a flower is infected with the *Agrobacterium* transformant such that the plant is transformed therewith. Specifically, it is preferable that the target plant is capable of undergoing *Agrobacterium*. infection at least in the above-ground part of the plant.

Hereinafter, the present invention will be explained in detail with reference to an exemplary embodiment. This exemplary embodiment is an example of the best modes illustrative of the present invention. However, the scope of the present invention is not intended to be limited to the exemplary embodiment.

(Exemplary Embodiment)

Hereinafter, procedures for generating a transformed plant capable of emitting fluorescence that is due to a mature fluorescent protein, which is produced by recombinantly expressing a non-plant-derived fluorescent protein in the epidermal cell of a plant leaf or stem will be described specifically.

(Wild-Type Plant)

In the present exemplary embodiment, to generate the transformed plant, *Arabidopsis thaliana* belonging to the family Brassicaceae, which is one of dicotyledons, is used as a host plant for genetic recombination. Particularly, of wild-type strains of *Arabidopsis thaliana*, a standard strain Col-O is used.

Wild-type *Arabidopsis thaliana* is capable of undergoing *Agrobacterium* infection and producing a harvestable T1 seed through the self-pollination of each plant individual, so that it is used in the process for generation of the transformed plant, in which foreign gene DNA is recombined in the chromosomal DNA thereof using a Ti-plasmid system derived from a bacterium of the genus *Agrobacterium*.

(Host Bacterial Strain of Genus *Agrobacterium* for Preparation of Transformed *Agrobacterium*)

In the present exemplary embodiment, such procedure that the leaf/stem of wild-type *Arabidopsis thaliana* is infected with transformed *Agrobacterium* is employed. Therefore, *Agrobacterium tumefaciens* is selected as a host bacterial strain of the genus *Agrobacterium*. Specifically, electroporation is used in the step of introduction of a T-DNA-based binary vector described later. Therefore, an *Agrobacterium tumefaciens* GV3101 strain, particularly, an electro-competent cell of *Agrobacterium* GV3101, is used to prepare a transformant.

(T-DNA-Based Binary Vector)

In the Present Exemplary Embodiment, a T-DNA-Based binary vector pBIG2113SF is used in the step of transformation of the *Agrobacterium tumefaciens* GV3101 strain. This T-DNA-based binary vector pBIG2113SF is obtained by introducing two SfiI restriction sites as a cloning site into a T-DNA-based binary vector pBIG2113N (see Taji, T. et al., Plant J., 24 (4), p. 417-426 (2002)) comprising a promoter for constitutive expression. Accordingly, the T-DNA-based binary vector pBIG2113SF comprises an *E. coli* replication origin ORI from *E. coli* plasmid pBR322 and *Agrobacterium* replication origin ORI from an *Agrobacterium tumefaciens* Ti-plasmid, which are both present in the T-DNA-based binary vector pBIG2113N. Moreover, the T-DNA-based binary vector pBIG2113SF comprises a drug resistance gene, specifically, a kanamycin resistance gene (Km$^r$), as a marker gene used for confirming the introduction of the *E. coli*/ *Agrobacterium* binary vector into *E. coli* or *Agrobacterium*.

On the other hand, the promoter for constitutive expression, a polyadenylation signal sequence, and a terminator are provided in a region flanked by two T-DNA border nucleotide sequences on the upward and downward sides, which are derived from the T-DNA region in the Ti-plasmid. The cloning site is formed between the promoter for constitutive expression and the polyadenylation signal sequence/terminator. As the vector pBIG2113SF is derived from pBIG2113N, a cauliflower mosaic virus 35S promoter sequence (see Sanders, P. R. et al., Nucleic Acids Res., 15 (4), p. 1543-58 (1987)) is employed as the promoter for constitutive expression therein. Specifically, the foreign gene is introduced through homologous replacement-based genetic recombination into the chromosomal gene of the host plant by using the border nucleotide sequences at both ends of the T-DNA region, so that the gene is constitutively transcribed by the promoter for constitutive expression.

In addition, in the region flanked by the border nucleotide sequences at both ends of the T-DNA region, a second drug resistance gene, specifically, a hygromycin resistance gene, is incorporated in advance as a marker gene used for confirming the success of genetic recombination in the host plant.

On the other hand, the cloning site provided in the T-DNA-based binary vector pBIG2113SF is composed two SfiI restriction sites, which have restriction enzyme recognition sites of 8-base or longer. Therefore, the direction of a DNA fragment inserted in this cloning site is limited to one direction. Thus, the aimed DNA fragment can be inserted selectively in the direction where the sense strand of the foreign gene present in the inserted DNA fragment undergoes transcription under the control of the promoter for constitutive expression.

The T-DNA-based binary vector pBIG2113SF is free from a Vir region containing gene clusters involved in the process for performing the homologous replacement-based recombinant introduction of the region flanked by the border nucleotide sequences at both ends of the T-DNA region into the chromosomal DNA of the host plant. Accordingly, the aimed foreign gene is inserted into the cloning site in the T-DNA-based binary vector pBIG2113SF to construct a plasmid vector for Agrobacterium transformation, and then, this plasmid vector for transformation is introduced into the host strain GV3101 having a Ti-plasmid. In the obtained Agrobacterium transformant, homologous replacement-based recombination presumably occurs between the T-DNA region of the Ti-plasmid and the T-DNA region in the introduced plasmid vector for transformation. Thus, a recombinant Ti-plasmid that contains the Vir region derived from the Ti-plasmid of the host Agrobacterium and the T-DNA region comprising the insert of the foreign gene is presumably formed in the cell of the transformed Agrobacterium.

As a result, it is presumed that the host plant is infected with this Agrobacterium transformant such that the introduction of the T-DNA region comprising the insert of the foreign gene into the chromosomal DNA of the plant is promoted by products expressed from the genes of the gene clusters VirA, VirB, VirC, VirD, VirE, and VirG present in the Vir region in the recombinant Ti-plasmid.

(Construction of T-DNA-Based Binary Vector Comprising Insert of DNA Encoding Full-Length Amino Acid Sequence of Wild-Type CpYGFP)

First, a DNA fragment comprising SfiI restriction sites respectively added upward and downward of DNA encoding the full-length amino acid sequence of wild-type CpYGFP is prepared according to the following procedure.

PCR reaction is performed using, as a template, the cDNA fragment having the nucleotide sequence of SEQ ID NO: 2 and encoding the full-length amino acid sequence of CpYGFP, which has been cloned in pBluescriptII SK-NFP, and using a primer pair having the following sequences:

a forward primer; primer GS17:

```
                                    (SEQ ID NO. 10)
5'-GTACGTATTTTTACAACAATTACCAAC-3'
``` a reverse primer; primer-GS18:

```
                                    (SEQ ID NO. 11)
5'-GGATTCAATCTTAAGAAACTTTATTGC-3'
``` to prepare a PCR amplification product in which the SfiI restriction sites have been introduced respectively upward and downward of the DNA encoding the full-length amino acid sequence of the wild-type CpYGFP. This PCR reaction is performed under conditions shown below using the pBluescriptII SK-NFP as a template and using a commercially available PCR kit.

TABLE 2-1

Temperature conditions for PCR reaction:
Apparatus used: Mastercycler Gradient (Eppendorf)

| Cycle operation | Temperature (° C.) | Time | |
|---|---|---|---|
| denature | 95 | 7 min | |
| anneal | 58 | 30 sec | |
| extention | 68 | 1 min | 40 times |
| denature | 94 | 30 sec | |
| extention | 72 | 3 min 30 sec | |
| store | 4 | Overnight (14 hrs) | |

TABLE 2-2

Composition of reaction solution

| Component | Concentration of stock solution | Mixed amount (µL) |
|---|---|---|
| H₂O (distilled water) | | 18.4 |
| 10 x Buffer | 10 x | 3 |
| dNTP | 2 mM | 3 |
| rTaq DNA Pol. | 5 u/µL | 0.3 |
| GS17 | 100 µM | 0.15 |
| GS18 | 100 µM | 0.15 |
| Template plasmid | 12-17 ng/µL | 5 |
| Total | | 30.0 |

The prepared PCR amplification product is a DNA fragment of 782 bp in total that comprises: the 660-bp portion corresponding to ORF in the cDNA encoding the full-length amino acid sequence of the wild-type CpYGFP; on the 5' terminal side thereof, a noncoding region of approximately 40 bp comprising the SfiI restriction site; and on the 3' terminal side thereof, a noncoding region of approximately 80 bp comprising the SfiI restrict-on site.

Meanwhile, a short DNA fragment with two SfiI restriction sites included therein is incorporated into an XbaI site present in the multicloning site of a commercially available vector pBluescript II SK(+) (purchased from Stratagene) to prepare a modified pBluescript cloning vector.

Subsequently, the DNA fragment encoding the full-length amino acid sequence of the wild-type CpYGFP, in which the SfiI restriction sites have been introduced on the 5' and 3' terminal sides thereof, is inserted to between these two SfiI restriction sites in the modified pBluescript cloning vector. The obtained plasmid vector is temporarily introduced into E. coli to prepare a transformant. This transformant is cultured, and multified plasmids are collected. The collected plasmid vector is prepared into a plasmid solution having a DNA concentration of 250 ng/µL. This plasmid vector is called a subcloning vector pBluescript-CpYGFP comprising the insert of the DNA fragment encoding the full-length amino acid sequence of the wild-type CpYGFP between the two SfiI restriction sites in the modified pBluescript cloning vector.

The DNA fragment encoding the full-length amino acid sequence of the wild-type CpYGFP, which has both ends serving as ends for digestion with the restriction enzyme SfiI, is collected from the vector pBluescript-CpYGFP according to the following procedure. The restriction enzyme SfiI and a buffer solution component 10×M Buffer used in the following reaction solution for digestion reaction using the restriction enzyme are purchased from the distributor: Takara Bio Inc.

TABLE 3-1

Composition of initial reaction solution for the first digestion reaction using the restriction enzyme SfiI

| Component | Concentration of stock solution | Mixed amount (µL) |
|---|---|---|
| H$_2$O (distilled water) | | 7 |
| 10 x Buffer | 10 x | 1 |
| SfiI enzyme solution | 10 u/µL | 1.5 |
| pBluescript-CpYGFP | 250 ng/µL | 0.5 |
| Total | | 10.0 |

The initial reaction solution is kept at 50° C. for 3 hours to cause enzyme reaction. Subsequently, to the reaction solution, 0.5 µL of the SfiI enzyme solution is added, and then, the mixture is further kept at 50° C. for 2 hours to continue the enzyme reaction. Then, the enzymatically digested DNA is precipitated using isopropanol and collected from the reaction solution. The collected DNA is redissolved in 5 µL of distilled water.

In the first digestion reaction, a portion may remain, which has undergone incomplete cleavage with the restriction enzyme SfiI. To complete the cleavage of the remaining portion, second digestion reaction is performed according to the following procedure.

TABLE 3-2

Composition of initial reaction solution for the second digestion reaction using the restriction enzyme SfiI

| Component | Concentration of stock solution | Mixed amount (µL) |
|---|---|---|
| H$_2$O (distilled water) | | 3.5 |
| 10 x Buffer | 10 x | 1 |
| SfiI enzyme solution | 10 u/µL | 0.5 |
| Redissolved DNA solution | | 5 |
| Total | | 10.0 |

The initial reaction solution is kept at 50° C. for 2 hours to cause enzyme reaction. Then, the enzymatically digested DNA is precipitated using isopropanol and collected from the reaction solution. The collected DNA is redissolved in 0.5 µL of distilled water.

In similar, for the T-DNA-based binary vector pBIG2113SF, the two SfiI restriction sites present in the cloning site thereof are cleaved with the restriction enzyme SfiI according to the following procedure.

TABLE 4-1

Composition of initial reaction solution for the first digestion reaction using the restriction enzyme SfiI

| Component | Concentration of stock solution | Mixed amount (µL) |
|---|---|---|
| H$_2$O (distilled water) | | 7.5 |
| 10 x Buffer | 10 x | 1 |
| SfiI enzyme solution | 10 u/µL | 0.5 |
| pBIG2113SF | 2 ng/µL | 1 |
| Total | | 10.0 |

The initial reaction solution is kept at 50° C. for 3 hours to cause enzyme reaction. Subsequently, to the reaction solution, 0.5 µL of the SfiI enzyme solution is added, and then, the mixture is further kept at 50° C. for 2 hours to continue the enzyme reaction. Then, the enzymatically digested DNA is precipitated using isopropanol and collected from the reaction solution. The is collected DNA is redissolved in 5 µL of distilled water.

In the first digestion reaction, a portion may remain, which has undergone incomplete cleavage with the restriction enzyme SfiI. To complete the cleavage of the remaining portion, second digestion reaction is performed according to the following procedure.

TABLE 4-2

Composition of initial reaction solution for the second digestion reaction using the restriction enzyme SfiI

| Component | Concentration of stock solution | Mixed amount (µL) |
|---|---|---|
| H$_2$O (distilled water) | | 3.5 |
| 10 x Buffer | 10 x | 1 |
| SfiI enzyme solution | 10 u/µL | 0.5 |
| Redissolved DNA solution | | 5 |
| Total | | 10.0 |

The initial reaction solution is kept at 50° C. for 2 hours to cause enzyme reaction. Then, the enzymatically digested DNA is precipitated using isopropanol and collected from the reaction solution. The collected DNA is redissolved in 0.5 µL of distilled water.

Figure 11:
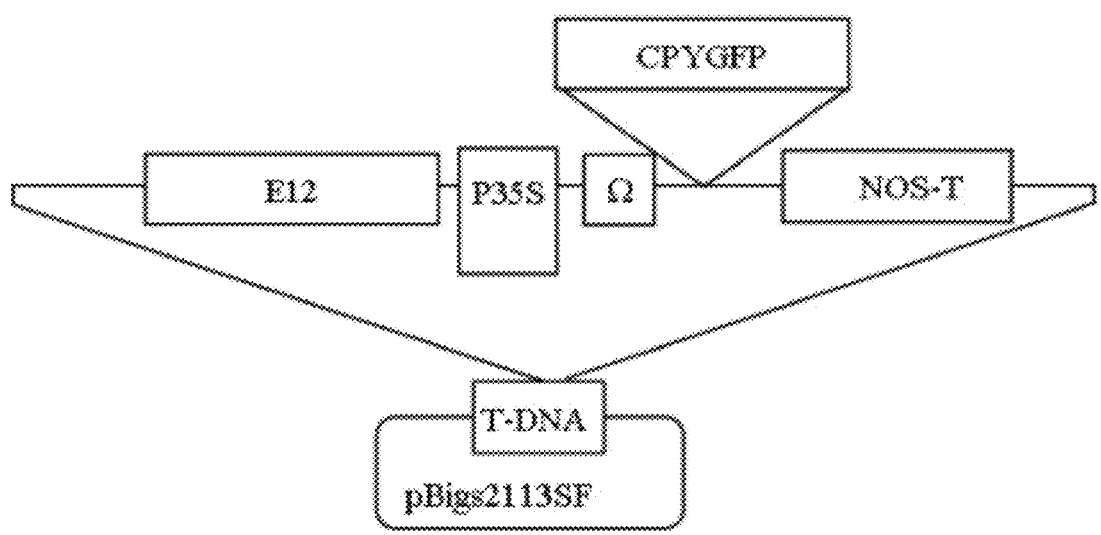
FIG. 11 is a diagram schematically showing the construction of a T-DNA-based binary vector pBIG2113SF in which DNA encoding the full-length amino acid sequence of the wild-type CpYGFP has been inserted using two SfiI restriction sites present in the cloning site of the T-DNA-based binary vector.

The DNA fragment encoding the full-length amino acid sequence of the wild-type CpYGFP with both ends serving as ends for digestion with the restriction enzyme SfiI, which is prepared in advance by treatment of enzymatic digestion by restriction enzyme SfiI, is ligated with the linearized vector fragment of pBIG2113SF through ligation reaction according to the following procedure to construct a T-DNA-based binary vector comprising the insert of the DNA encoding the full-length amino acid sequence of the wild-type CpYGFP. The construction of the T-DNA-based binary vector is schematically shown in FIG. 11.

This ligation reaction is performed under the following conditions. T4 ligase and a reaction buffer solution used are included in a commercially available enzyme kit (New England Biolabs).

TABLE 4-3

Composition of reaction solution for ligation reaction

| Component | Concentration of stock solution | Mixed amount (μL) |
|---|---|---|
| H₂O (distilled water) | | 0.5 |
| 10 x Buffer | 10 x | 0.2 |
| T4 ligase enzyme solution | 400 u/μL | 0.2 |
| Soln. of DNA fragment to be inserted | | 0.5 |
| Soln. of vector fragment | | 0.5 |
| Total | | 2.0 |

This reaction solution is kept overnight (14 hours) at 16° C. to ligate the ends enzymatically digested with the restriction enzyme SfiI using the T4 ligase enzyme. After this reaction, the reaction solution is directly used in the transformation of E. coli by the introduction of the T-DNA-based binary vector comprising the insert of the DNA encoding the full-length amino acid sequence of the wild-type CpYGFP.

(Screening by Colony PCR to Select E. Coli Clones that Retain Binary Vector Comprising Insert of the Aimed DNA)

E. coli is transformed using the solution containing the constructed T-DNA-based binary vector comprising the insert of the DNA encoding the full-length amino acid sequence of the wild-type CpYGFP. The introduction of the binary vector into E. coli is performed using electroporation. To 20 μL of a suspension of an electro-competent cell of an E. coli DH10B strain (Invitrogen), a 0.5 μL aliquot of the ligation reaction solution is added, and then, the mixture is placed in a cell for electroporation and subjected to electroporation treatment.

After treatment, the host E. coli DH10B strain is cultured on an agar medium containing 50 mg/L kanamycin to form colonies. The kanamycin resistance gene (Km$^r$) is provided as a marker gene in the T-DNA-based binary vector used in the step of transformation. Therefore, it is judged that, in each colony that exhibits this kanamycin resistance, the T-DNA-based binary vector is introduced therein, and thus, the kanamycin resistance gene included in the binary vector is expressed therein.

The ligation reaction solution contains a T-DNA-based binary vector free from the insert of the aimed DNA fragment in the cloning site, in addition to the T-DNA-based binary vector comprising the insert of the aimed DNA encoding the full-length amino acid sequence of the wild-type CpYGFP. Thus, each colony that exhibits the kanamycin resistance is screened by colony PCR to select a transformant that actually retains the T-DNA-based binary vector comprising the insert of the aimed DNA encoding the full-length amino acid sequence of the wild-type CpYGFP.

In this screening by colony PCR, PCR reaction is performed under conditions described in Tables 5-1 and 5-2 below using, as a template, the DNA of the transformant as the formed colony to confirm the presence or absence of a PCR amplification product corresponding to the inserted DNA fragment. The transformant as the formed colony is collected, and then subjected to lysis. The lysate is added to the following reaction solution, and PCR amplification reaction is performed using DNA contained in the bacterial cell as a template.

In the step, used as primers for PCR are respectively primers having the following sequences:

as a upward primer, primer GS17:

```
                                    (SEQ ID NO. 10)
5'-GTACGTATTTTTACAACAATTACCAAC-3'
``` as a downward primer, primer GS18;

```
                                    (SEQ ID NO. 11)
5'-GGATTCAATCTTAAGAAACTTTATTGC-3'
```

TABLE 5-1

Temperature conditions for PCR reaction:
Apparatus used: Mastercycler Gradient (Eppendorf)

| Cycle operation | Temperature (° C.) | Time | |
|---|---|---|---|
| denature | 95 | 7 min | |
| anneal | 58 | 30 sec | |
| extention | 68 | 1 min | 40 times |
| denature | 94 | 30 sec | |
| extention | 72 | 3 min 30 sec | |
| store | 4 | Overnight (14 hrs) | |

TABLE 5-2

Composition of reaction solution

| Component | Concentration of stock solution | Mixed amount (μL) |
|---|---|---|
| H₂O (distilled water) | | 23.4 |
| 10 x Buffer | 10 x | 3 |
| dNTP | 2 mM | 3 |
| rTaq DNA Pol. | 5 u/μL | 0.3 |
| GS17 | 100 μM | 0.15 |
| GS18 | 100 μM | 0.15 |
| Colony Soln. | | 1 |
| Total | | 31.0 |

After PCR amplification, an aliquot (5 μL) of the reaction solution is collected and electrophoresed to analyze the presence or absence of the PCR amplification product and the size thereof.

Of the colonies that exhibit kanamycin resistance, 33 colonies are selected at random and divided into 11 groups (group Nos. 1 to 11) in total each containing 3 colonies. Whether or not each group contains a colony in which the T-DNA-based binary vector comprising the insert of the aimed DNA encoding the full-length amino acid sequence of the wild-type CpYGFP has been introduced is confirmed. Specifically, small amounts of the bacterial cells are collected from the 3 colonies constituting each group and mixed, and PCR amplification reaction is performed according to the conditions described above. As a result, the aimed PCR amplification product corresponding to the nucleotide length of 742 bp derived from the DNA fragment encoding the full-length amino acid sequence of the wild-type CpYGFP was found in all the groups.

Next, of the groups in which only the PCR amplification product corresponding to the nucleotide length of 742 bp was clearly confirmed, 9 colonies in total from three groups of group Nos. 8, 10, and 11 were separately subjected to single colony PCR. As a result, the PCR amplification product corresponding to the nucleotide length of 742 bp was found in 8 colonies of clone Nos. 8-4, 8-5, 8-6, 10-7, 10-8, 11-1, 11-2, and 11-3.

Specifically, at least clone Nos. 8-4, 8-5, 8-6, 10-7, 10-8, 11-1, 11-2, and 11-3 exhibit kanamycin resistance and provide the aimed PCR amplification product corresponding to the nucleotide length of 742 bp derived from the DNA fragment encoding the full-length amino acid sequence of the wild-type CpYGFP. Therefore, these clones were selected as E. coli transformants in which the T-DNA-based binary vector comprising the insert of the aimed DNA encoding the full-length amino acid sequence of the wild-type CpYGFP has been introduced.

(Subculture of Each E. Coli Clone and Collection of Amplified Binary Vectors Therefrom)

The transformed E. coli collected from each of the selected eight E. coli clones of Nos. 8-4, 8-5, 8-6, 10-7, 10-8, 11-1, 11-2, and 11-3 that retain the binary vector comprising the insert of the aimed DNA is inoculated on 4 mL of the LB medium supplemented with 50 ppm kanamycin such that the transformed E. coli is proliferated to amplified the plasmid vector. After inoculation, at a point in time when the transformed E. coli is cultured at 37° C. for 18 hours, the culture is terminated, and the bacterial cell is collected by centrifugation. The collected bacterial cell is washed with 20 mM Tris-HCl pH 8.5, and then, the collected transformed E. coli is subjected to lysis. The DNA is collected therefrom, and the aimed circular DNA molecule (plasmid vector) having the molecular weight of approximately 14 kbp is isolated and purified therefrom.

The solution containing the plasmid of approximately 14 kbp collected from the subculture of each E. Coli clone is measured for its DNA content. The result is shown in Table 5-3.

TABLE 5-3

Concentration of collected plasmid (binary vector) included in the solution:

| Transformed E. coli clone | $OD_{260}$ | $OD_{280}$ | $OD_{320}$ | DNA concentration ng/μL |
|---|---|---|---|---|
| No. 8-4 | 37.10 | 18.7 | <0.001 | 50 |
| No. 8-5 | 46.0 | 26.6 | <0.001 | 45 |
| No. 8-6 | 49.0 | 29.0 | <0.001 | 36 |
| No. 10-7 | 50.8 | 27.7 | <0.001 | 36 |
| No. 10-8 | 45.0 | 23.6 | <0.001 | 37 |
| No. 11-1 | 36.9 | 18.3 | <0.001 | 36 |
| No. 11-2 | 36.9 | 19.0 | <0.001 | 46 |
| No. 11-3 | 37.3 | 19.1 | <0.001 | 49 |

(Plasmid PCR and Confirmation of Nucleotide Sequence of Inserted DNA Fragment by Sequencing of Obtained PCR Product)

An aliquot of the solution containing the binary vector comprising the insert of the aimed DNA, which has been collected from the subculture of each E. coli clone, is diluted 3-fold and then subjected to actual sequencing as to the nucleotide sequence between the two SfiI restriction sites in the binary vector. Specifically, this sequencing is performed to confirm that the DNA encoding the full-length amino acid sequence of the wild-type CpYGFP is inserted in a sense direction from the upward SfiI site A toward the downward SfiI site B.

First, the DNA fragment inserted between the two SfiI restriction sites is amplified by PCR using the collected binary vector (plasmid) as a template. The collected plasmid solution is diluted 3-fold. This 3-fold diluted solution is used to perform PCR amplification under conditions shown in Tables 6-1 and 6-2 below. Used as primers for PCR are respectively primers having the following sequences:

as an upward primer, primer GS17:

(SEQ ID NO. 10)
5'-GTACGTATTTTTACAACAATTACCAAC-3' as a downward primer, primer GS18:

(SEQ ID NO. 11)
5'-GGATTCAATCTTAAGAAACTTTATTGC-3'

TABLE 6-1

Temperature conditions for PCR reaction:
Apparatus used: Mastercycler Gradient (Eppendorf)

| Cycle operation | Temperature (° C.) | Time | |
|---|---|---|---|
| denature | 95 | 7 min | |
| anneal | 58 | 30 sec | |
| extention | 68 | 1 min | 40 times |
| denature | 94 | 30 sec | |
| extention | 72 | 3 min 30 sec | |
| store | 4 | Overnight (14 hrs) | |

TABLE 6-2

Composition of reaction solution

| Component | Concentration of stock solution | Mixed amount (μL) |
|---|---|---|
| $H_2O$ (distilled water) | | 18.4 |
| 10 x Buffer | 10 x | 3 |
| dNTP | 2 mM | 3 |
| rTaq DNA Pol. | 5 u/μL | 0.3 |
| GS17 | 100 μM | 0.15 |
| GS18 | 100 μM | 0.15 |
| Template plasmid | 12-17 ng/μL | 5 |
| Total | | 30.0 |

Figure 5:
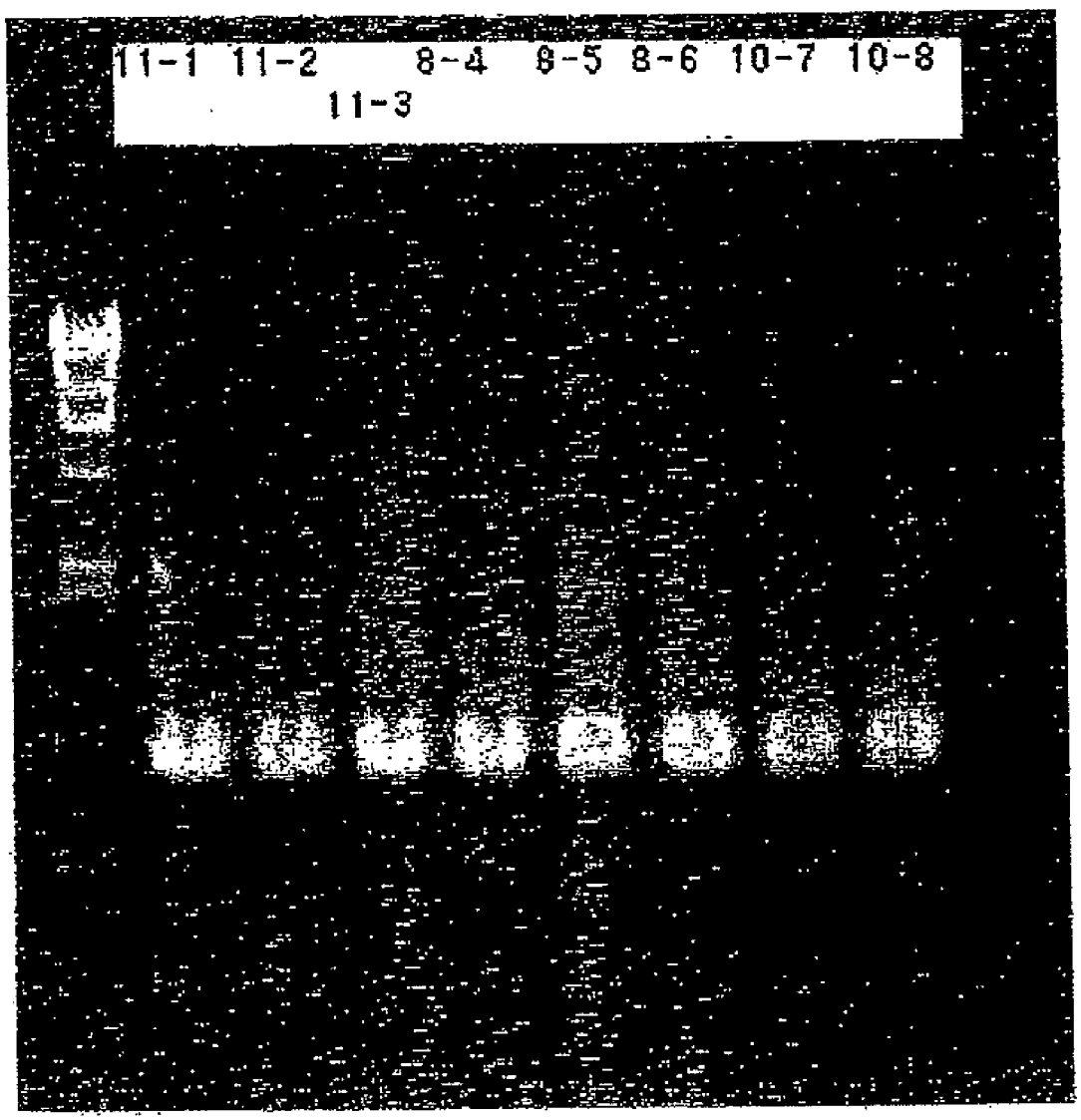
FIG. 5 shows results, wherein regarding *E. coli* colonies 11-1, 11-2, 11-3, 8-4, 8-5, 8-6, 10-7, and 10-8 from which a PCR product corresponding to a DNA fragment encoding the full-length amino acid sequence of the GFP-like fluorescent protein CpYGFP has been obtained in a single colony PCR method, a plasmid is extracted from each *E. coli* colony, and a plasmid PCR method is performed using the extracted plasmid as a template to confirm that a PCR product corresponding to the DNA fragment encoding the full-length amino acid sequence of the GFP-like fluorescent protein CpYGFP is obtained.

After PCR amplification, an aliquot of the reaction solution is collected and electrophoresed to analyze the size of the PCR amplification product. A band of the PCR amplification product with a size corresponding to the size of 742 bp of the DNA fragment to be inserted is clearly observed, as shown in FIG. 5, in all the plasmids collected from the 8 clones of clone Nos. 8-4, 8-5, 8-6, 11-1, 11-2, 11-3, 10-7, and 10-8.

To confirm the nucleotide sequence of the PCR amplification product contained in each prepared plasmid vector, the DNA fragment is amplified by another PCR using the PCR-amplified region as a template to prepare a sample for sequencing.

In the step, as a forward primer, primer GS17:

(SEQ ID NO. 10)
5'-GTACGTATTTTTACAACAATTACCAAC-3' and as a reverse primer, primer GS18:

(SEQ ID NO. 11)
5'-GGATTCAATCTTAAGAAACTTTATTGC-3' are used as primers for the sequencing to prepare a single-stranded amplification product from the region of 742 bp in nucleotide length as a template. The sample for sequencing prepared for analyzing the nucleotide sequence of the DNA fragment portion of 742 bp is collected as a pellet according to a standard method by adding isopropanol to the PCR reaction solution such that the single-stranded DNA as the amplification product is precipitated. The collected single-stranded-DNA as the amplification product is redissolved in a buffer solution and used as the sample for sequencing.

The sample for sequencing prepared from the DNA fragment portion of 742 bp is applied to a commercially available sequencer ABI PRISM 310 Genetic Analyzer to respectively conduct sequencing from the 5' end and sequencing from the 3' end.

The results of sequencing from the 5' end and sequencing from the 3' end are integrated to confirm that the nucleotide sequence of the DNA fragment inserted in the cloning site between the two SfiI restriction sites has the aimed nucleotides encoding the full-length amino acid sequence of the CpYGFP and is free from errors that occur during PCR amplification.

In this case, the binary vectors collected from 5 clones of Nos. 8-4, 8-5, 11-3, 10-7, and 10-8, of the 8 clones of Nos. 8-4, 8-5, 8-6, 11-1, 11-2, 11-3, 10-7, and 10-8, are sequenced to confirm the nucleotide sequence of the inserted DNA fragment. As a result, it was confirmed that in the binary vectors collected from 4 clones of Nos. 8-4, 8-5, 11-3, and 10-7, the DNA encoding the full-length amino acid sequence of the wild-type CpYGFP was actually inserted in a sense direction from the upward SfiI site A toward the downward SfiI site B.

(Preparation of *Agrobacterium* Transformant by Introduction of T-DNA-Based Binary Vector)

*Agrobacterium* transformants are prepared using the binary vectors of Nos. 8-4 and 11-3 that have been confirmed as binary vectors actually having the insert of the aimed DNA in the intended direction as a result of the sequencing. The introduction of the binary vector into a bacterium of the genus *Agrobacterium* is performed using electroporation. To 40 μL of a suspension of an electro-competent cell of *Agrobacterium* GV3101, a 2 μL aliquot of the collected solution of each binary vector is added, and then, the mixture is placed in a cell for electroporation and subjected to electroporation treatment.

After treatment, the *Agrobacterium* strain is cultured on an agar medium containing 50 ppm kanamycin to form colonies. The aimed DNA is inserted in advance in the intended direction in the binary vector used in the transformation. Therefore, it is judged that in each colony that exhibits the kanamycin resistance, the used binary vector is introduced therein, and the kanamycin resistance gene containen in the binary vector is expressed.

The transformant in which the binary vector of No. 8-4 or 11-3 has been introduced is cultured, and their respective colonies on the agar medium are collected and suspended in the LB liquid medium. An aliquot of this *Agrobacterium* transformant suspension is used as an inoculum solution. Glycerol is added at a final concentration of 15% to the remainder of the *Agrobacterium* transformant suspension, and then, the solution is stored at −80° C.

(Generation of Transformed Plant by Infection with *Agrobacterium* Transformant)

The inoculum of the *Agrobacterium* transformant is inoculated on 200 mL of an LB medium supplemented with 50 mg/L kanamycin, and shake-cultured overnight. The bacterial cell is collected from the obtained culture solution. The collected bacterial cell is suspended in an MS medium supplemented with 5% sucrose to prepare a bacterial cell suspension.

In this case, bacterial cell suspensions of transformant Nos. 8-4 and 11-3 prepared by introducing the binary vectors of Nos. 8-4 and 11-3, respectively, are used in the transformation of a plant.

A wild-type strain Col-O of *Arabidopsis thaliana* obtained by inoculating a seed in soil and then cultivating it for approximately 1.5 months is used as the plant to be infected. Each bacterial cell suspension is sprayed onto the above-ground part of the grown plant such that the meristem of the above-ground part of the plant is infected with the *Agrobacterium* transformant.

The plant thus infected is further cultivated for 2 months in isolation from other plants. Each individual of the plant is subjected to self-pollination, and a $T_1$ seed is harvested from the plant individual. The T1 seed collected from the plant individual is stored in a separate container 0.5 g of the T1 seed collected from the plant individual is inoculated on absorbent cotton dipped in an aqueous medium for germination supplemented with hygromycin at a concentration of 20 ppm. A seedling geminated therefrom on the hygromycin selective medium retains a hygromycin resistance gene as a selection marker. The seedling selected by the primary screening based on the presence or absence of this hygromycin resistance is further cultivated for approximately 2 weeks and transplanted into soil in a pot at the time when a true leaf has come out.

Figure 6:
FIG. 6 shows a printed-out of image recorded by digital camera, wherein a T1 seed collected from *Arabidopsis thaliana* infected by a floral dipping method with *Agrobacterium* transformed with the binary vector 11-3 is inoculated on a selective medium supplemented with hygromycin and screened for the presence or absence of hygromycin resistance based on the success or failure of germination and subsequent growth, and then, an individual (11-3-3) that exhibits hygromycin resistance is transplanted into usual soil in a pot and observed for its overall outline on exposure to a daylight source at the stage when true leaves have come out. In the same pot, a wild-type strain of *Arabidopsis thaliana* is transplanted as a reference and compared therewith in overall appearance profile.
Figure 7:
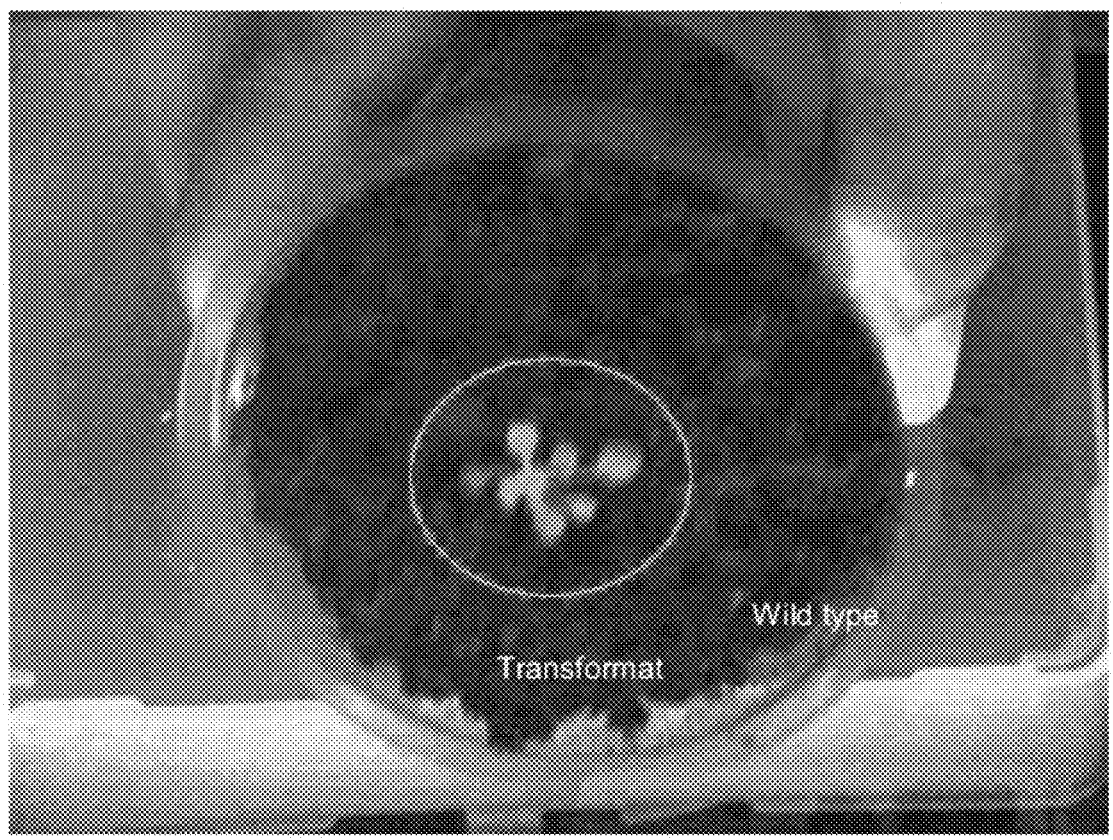
FIG. 7 shows a printed-out of image recorded by digital camera, wherein the individual (11-3-3) that exhibits hygromycin resistance, which is shown in FIG. 6, is transplanted into usual soil in a pot and observed for recombinantly expressed CpYGFP-derived fluorescence emitted from the surface of its true leaf on exposure to dark light (UV light source) at the stage when the true leaves have come out.

At this time, individuals that emit yellow-green fluorescence specific to the wild-type CpYGFP are selected with the epidermis of the true leaf exposed to dark light. Among the selected individuals that emit yellow-green fluorescence specific to the wild-type CpYGFP on exposure to dark light, a plant individual (11-3-3) grown from the T1 seed, which is derived from the plant transformed with the transformant No. 11-3, is observed by comparison with a plant individual grown from a wild-type Col-O seed on exposure to usual white light. The results are shown in FIG. 6. Moreover, these plant individuals are observed by comparison on exposure to dark light in the dark. The results are shown in FIG. 7. The selected plant individual (11-3-3) is confirmed to emit yellow-green fluorescence from the epidermis of the leaf on exposure to dark light in the dark. On the other hand, the wild-type Col-O plant individual cannot be recognized on exposure to dark light in the dark.

An individual secondarily selected by phenotypic screening for confirming the recombinant expression of the wild-type CpYGFP in the epidermal cell of the leaf is further cultivated for 3 months in isolation from other individuals. Each individual of the plant is subjected to self-pollination, and a T2 seed is harvested from the plant individual.

Plural plant individuals secondarily selected by the phenotypic screening are grown. The appearance profiles of the plants are observed by comparison on exposure to usual white light at the time when they reach the stage of petal formation. The results are shown in FIGS. 8(*a*) and 9(*a*). Moreover, they are observed by comparison on exposure to dark light in the dark. The results are shown in FIGS. 8(*b*) and 9(*b*). All the transformed plant individuals have no difference in appearance profile from the wild-type Col-O plant as long as they are observed on exposure to usual white light. On the other hand, the transformed plant individuals are confirmed to emit yellow-green fluorescence from the epidermis of the leaf/stem and petal, when observed on exposure to dark light in the dark.

Among 6 individuals of seedlings selected by the primary screening based on the presence or absence of hygromycin resistance from the T1 seeds derived from the plant transformed with the transformant No. 11-3, 3 plant individuals were secondarily selected by the phenotypic screening. Moreover, among 24 individuals of seedlings selected by the primary screening based on the presence or absence of hygromycin resistance from the T1 seeds derived from the plant transformed with the transformant No. 8-4, 17 plant individuals were secondarily selected by the phenotypic screening.

Industrial Applicability

The present invention can be used preferably for generating a transformed plant capable of emitting fluorescence, particularly, for generating a transformed garden plant that is capable of emitting fluorescence with high efficiency even in plant organs containing a large amount of chlorophyll, such as leaves.

---

The invention claimed is:

1. A method for using a *Chiridius poppei*-derived fluorescent protein for generation of a transformed plant capable of emitting fluorescence, characterized in that
said *Chiridius poppei*-derived fluorescent protein used therefor is a *Chiridius poppei*-derived wild-type yellowish-green fluorescent protein (CpYGFP) comprising the following amino acid sequence (SEQ ID NO: 1):

```
MTTFKIESRI HGNLNGEKFE LVGGGVGEEG RLEIEMKTKD KPLAFSPFLL SHCMGYGFYH    60

FASFPKGTKN IYLHAATNGG YTNTRKEIYE DGGILEVNFR YTYEFNKIIG DVECIGHGFP   120

SQSPIFKDTI VKSCPTVDLM LPMSGNIIAS SYARAFQLKD GSFYTAEVKN NIDFKNPIHE   180

SFSKSGPMFT HRRVEETHTK ENLAMVEYQQ VFNSAPRDM                         219
``` as its full-length amino acid sequence,
a wild-type plant used in the process for generation of the aimed transformed plant capable of emitting fluorescence is a plant which is capable of undergoing *Agrobacterium* infection and producing a harvestable T1 seed through the self-pollination of each plant individual, and the process for generation of the aimed transformed plant capable of emitting fluorescence comprises steps of:

inserting a DNA fragment encoding the full-length amino acid sequence of the *Chiridius poppei*-derived fluorescent protein into the cloning site of a T-DNA-based binary vector;

introducing the obtained T-DNA-based binary vector into a host bacterium of the genus *Agrobacterium* such that the bacterium of the genus *Agrobacterium* is transformed therewith;

infecting the wild-type plant with the obtained transformant of the bacterium of the genus *Agrobacterium* such that a T-DNA region contained in the T-DNA-based binary vector is recombinantly introduced in the chromosomal DNA of the wild-type plant to obtain a transformed plant;

subjecting each individual of the obtained transformed plant to self-pollination, and then harvesting a T1 seed from the plant individual; and sowing the obtained T1 seed and screening each grown plant to select a transformed plant individual to which a fluorescent phenotype attributed to the recombinant expression of the fluorescent protein in the leaf surface of the plant has been imparted.

2. The method of using the *Chiridius poppei*-derived fluorescent protein according to claim 1, wherein the DNA fragment encoding the full-length amino acid sequence of the *Chiridius poppei*-derived fluorescent protein comprises the following nucleotide sequence (SEQ ID NO: 2):

```
ATG ACA ACC TTC AAA ATC GAG TCC CGG ATC CAT GGC AAC CTC AAC GGG    48
GAG AAG TTC GAG TTG GTT GGA GGT GGA GTA GGT GAG GAG GGT CGC CTC    96
GAG ATT GAG ATG AAG ACT AAA GAT AAA CCA CTG GCA TTC TCT CCC TTC   144
CTG CTG TCC CAC TGC ATG GGT TAC GGG TTC TAC CAC TTC GCC AGC TTC   192
CCA AAG GGG ACT AAG AAC ATC TAT CTT CAT GCT GCA ACA AAC GGA GGT   240
TAC ACC AAC ACC AGG AAG GAG ATC TAT GAA GAC GGC GGC ATC TTG GAG   288
GTC AAC TTC CGT TAC ACT TAC GAG TTC AAC AAG ATC ATC GGT GAC GTC   336
GAG TGC ATT GGA CAT GGA TTC CCA AGT CAG AGT CCG ATC TTC AAG GAC   384
ACG ATC GTG AAG TCG TGT CCC ACG GTG GAC CTG ATG TTG CCG ATG TCC   432
GGG AAC ATC ATC GCC AGC TCC TAC GCT AGA GCC TTC CAA CTG AAG GAC   480
GGC TCT TTC TAC ACG GCA GAA GTC AAG AAC AAC ATA GAC TTC AAG AAT   528
CCA ATC CAC GAG TCC TTC TCG AAG TCG GGG CCC ATG TTC ACC CAC AGA   576
CGT GTC GAG GAG ACT CAC ACC AAG GAG AAC CTT GCC ATG GTG GAG TAC   624
CAG CAG GTT TTC AAC AGC GCC CCA AGA GAG ATG TAG                    660
``` as the nucleotide sequence of an open-reading frame encoding the full-length amino acid sequence.

3. A method for using a *Chiridius poppei*-derived fluorescent protein for generation of a transformed plant capable of emitting fluorescence, characterized in that said *Chiridius poppei*-derived fluorescent protein used therefor is a *Chiridius poppei*-derived modified yellowish-green fluorescent protein (CpYGFP H52F) comprising the following amino acid sequence (SEQ ID NO: 3):

```
MTTFKIESRI HGNLNGEKFE LVGGGVGEEG RLEIEMKTKD KPLAFSPFLL SFCMGYGFYH    60
FASFPKGTKN IYLHAATNGG YTNTRKEIYE DGGILEVNFR YTYEFNKIIG DVECIGHGFP   120
SQSPIFKDTI VKSCPTVDLM LPMSGNIIAS SYARAFQLKD GSFYTAEVKN NIDFKNPIHE   180
SFSKSGPMFT HRRVEETHTK ENLAMVEYQQ VFNSAPRDM                         219
``` as its full-length amino acid sequence, a wild-type plant used in the process for generation of the aimed transformed plant capable of emitting fluorescence is a plant which is capable of undergoing *Agrobacterium* infection and producing a harvestable T1 seed through the self-pollination of each plant individual, and the process for generation of the aimed transformed plant capable of emitting fluorescence comprises steps of:

inserting a DNA fragment encoding the full-length amino acid sequence of the *Chiridius poppei*-derived fluorescent protein into the cloning site of a T-DNA-based binary vector;

introducing the obtained T-DNA-based binary vector into a host bacterium of the genus *Agrobacterium* such that the bacterium of the genus *Agrobacterium* is transformed therewith;

infecting the wild-type plant with the obtained transformant of the bacterium of the genus *Agrobacterium* such that a T-DNA region contained in the T-DNA-based binary vector is recombinantly introduced in the chromosomal DNA of the wild-type plant to obtain a transformed plant;

subjecting each individual of the obtained transformed plant to self-pollination, and then harvesting a T1 seed from the plant individual; and sowing the obtained T1 seed and screening each grown plant to select a transformed plant individual to which a fluorescent phenotype attributed to the recombinant expression of the fluorescent protein in the leaf surface of the plant has been imparted.

4. The method for using the *Chiridius poppei*-derived fluorescent protein according to claim 3, wherein the DNA fragment encoding the full-length amino acid sequence of the *Chiridius poppei*-derived fluorescent protein comprises the following nucleotide sequence (SEQ ID NO: 4):

```
ATG ACA ACC TTC AAA ATC GAG TCC CGG ATC CAT GGC AAC CTC AAC GGG      48

GAG AAG TTC GAG TTG GTT GGA GGT GGA GTA GGT GAG GAG GGT CGC CTC      96

GAG ATT GAG ATG AAG ACT AAA GAT AAA CCA CTG GCA TTC TCT CCC TTC     144

CTG CTG TCC TTC TGC ATG GGT TAC GGG TTC TAC CAC TTC GCC AGC TTC     192

CCA AAG GGG ACT AAG AAC ATC TAT CTT CAT GCT GCA ACA AAC GGA GGT     240

TAC ACC AAC ACC AGG AAG GAG ATC TAT GAA GAC GGC GGC ATC TTG GAG     288

GTC AAC TTC CGT TAC ACT TAC GAG TTC AAC AAG ATC ATC GGT GAC GTC     336

GAG TGC ATT GGA CAT GGA TTC CCA AGT CAG AGT CCG ATC TTC AAG GAC     384

ACG ATC GTG AAG TCG TGT CCC ACG GTG GAC CTG ATG TTG CCG ATG TCC     432

GGG AAC ATC ATC GCC AGC TCC TAC GCT AGA GCC TTC CAA CTG AAG GAC     480

GGC TCT TTC TAC ACG GCA GAA GTC AAG AAC AAC ATA GAC TTC AAG AAT     628

CCA ATC CAC GAG TCC TTC TCG AAG TCG GGG CCC ATG TTC ACC CAC AGA     576

CGT GTC GAG GAG ACT CAC ACC AAG GAG AAC CTT GCC ATG GTG GAG TAC     624

CAG CAG GTT TTC AAC AGC GCC CCA AGA GAC ATG TAG                     660
``` as the nucleotide sequence of an open-reading frame encoding the full-length amino acid sequence.

5. The method for using the *Chiridius poppei*-derived fluorescent protein according to claim 1, wherein
any plant belonging to the family Brassicaceae, Poaceae, Solanaceae, or Leguminosae is selected as said wild-type plant used in the process for generation of the aimed transformed plant capable of emitting fluorescence.

6. The method for using the *Chiridius poppei*-derived fluorescent protein according to claim 1, wherein
Any of a rose, *Dianthus caryophyllus*, a chrysanthemum, *Gerbera* cvs., *Eustoma grandiflorum*, *Petunia×hybrida*, *Torenia fournieri*, *Nierembergia hippomanica*, garden verbena, *Calibrachoa*hybrid Cultivar, *Cyclamen persicum*, *Cactaceae*, and an orchid is selected as said wild-type plant used in the process for generation of the aimed transformed plant capable of emitting fluorescence.

7. The method for using the *Chiridius poppei*-derived fluorescent protein according to claim 1, wherein
*Agrobacterium tumefaciens* is selected as the host bacterium of the genus *Agrobacterium* used in the step of introducing the obtained T-DNA-based binary vector into the host bacterium of the genus *Agrobacterium* such that the bacterium of the genus *Agrobacterium* is transformed therewith.

8. The method for using the *Chiridius poppei*-derived fluorescent protein according to claim 7, wherein
An electro-competent cell of an *Agrobacterium* GV3101 strain is selected as said host bacterium of the genus *Agrobacterium*.

9. A process for generation of a transformed plant capable of emitting fluorescence using a *Chiridius poppei*-derived fluorescent protein which is recombinantly expressed by genetic recombination and intracellularly produced, characterized in that the *Chiridius poppei*-derived fluorescent protein used therefor is a *Chiridius poppei*-derived wild-type yellowish-green fluorescent protein (CpYGFP) comprising the following amino acid sequence (SEQ ID NO: 1):

```
MTTFKIESRI HGNLNGEKFE LVGGGVGEEG RLEIEMKTKD KPLAFSPFLL SHCMGYGFYH   60

FASFPKGTKN IYLHAATNGG YTNTRKEIYE DGGILEVNFR YTYEFNKIIG DVECIGHGFP  120

SQSPIFKDTI VKSCPTVDLM LPMSGNIIAS SYARAFQLKD GSFYTAEVKN NIDFKNPIHE  180

SFSKSGPMFT HRRVEETHTK ENLAMVEYQQ VFNSAPRDM                        219
``` as its full-length amino acid sequence,
a wild-type plant used in the process for generation of the aimed transformed plant capable of emitting fluorescence is a plant which is capable of undergoing *Agrobacterium* infection and producing a harvestable T1 seed through the self-pollination of each plant individual, and
the process for generation of the aimed transformed plant capable of emitting fluorescence comprises the steps of:
inserting a DNA fragment encoding the full-length amino acid sequence of the *Chiridius poppei*-derived fluorescent protein into the cloning site of a T-DNA-based binary vector;
introducing the obtained T-DNA-based binary vector into a host bacterium of the genus *Agrobacterium* such that the bacterium of the genus *Agrobacterium* is transformed therewith;
infecting the wild-type plant with the obtained transformant of the bacterium of the genus *Agrobacterium* such that a T-DNA region contained in the T-DNA-based binary vector is recombinantly introduced in the chromosomal DNA of the wild-type plant to obtain a transformed plant;

subjecting each individual of the obtained transformed plant to self-pollination, and then harvesting a T1 seed from the plant individual; and sowing the obtained T1 seed and screening each grown plant to select a transformed plant individual to which a fluorescent phenotype attributed to the recombinant expression of the fluorescent protein in the leaf surface of the plant has been imparted.

10. The process for generation of the transformed plant capable of emitting fluorescence according to claim 9, wherein a garden plant which is capable of undergoing *Agrobacterium* infection and producing a harvestable T1 seed through the self-pollination of each plant individual is selected as the wild-type plant used in the process for generation of the aimed transformed plant capable of emitting fluorescence.

11. The method for using the *Chiridius poppei*-derived fluorescent protein according to claim 3, wherein any plant belonging to the family Brassicaceae, Poaceae, Solanaceae, or Leguminosae is selected as said wild-type plant used in the process for generation of the aimed transformed plant capable of emitting fluorescence.

12. The method for using the *Chiridius poppei*-derived fluorescent protein according to claim 3, wherein any of a rose, *Dianthus caryophyllus*, a chrysanthemum, *Gerbera* cvs., *Eustoma grandiflorum, Petunia×hybrida, Torenia fournieri, Nierembergia hippomanica*, garden verbena, *Calibrachoa* hybrid Cultivar, *Cyclamen persicum*, Cactaceae, and an orchid is selected as said wild-type plant used in the process for generation of the aimed transformed plant capable of emitting fluorescence.

13. The method for using the *Chiridius poppei*-derived fluorescent protein according to claim 3, wherein

*Agrobacterium tumefaciens* is selected as the host bacterium of the genus *Agrobacterium* used in the step of introducing the obtained T-DNA-based binary vector into the host bacterium of the genus *Agrobacterium* such that the bacterium of the genus *Agrobacterium* is transformed therewith.

14. The method for using the *Chiridius poppei*-derived fluorescent protein according to claim 13, wherein an electro-competent cell of an *Agrobacterium* GV3101 strain is selected as said host bacterium of the genus *Agrobacterium*.

15. A process for generation of a transformed plant capable of emitting fluorescence using a *Chiridius poppei*-derived fluorescent protein which is recombinantly expressed by genetic recombination and intracellularly produced, characterized in that the *Chiridius poppei*-derived fluorescent protein used therefor is a *Chiridius poppei*-derived modified yellowish-green fluorescent protein (CpYGFP H52F) comprising the following amino acid sequence (SEQ ID NO: 3):

```
MTTFKIESRI HGNLNGEKFE LVGGGVGEEG RLEIEMKTKD KPLAFSPFLL SFCMGYGFYH   60
FASFPKGTKN IYLHAATNGG YTNTRKEIYE DGGILEVNFR YTYEFNKIIG DVECIGHGFP  120
SQSPIFKDTI VKSCPTVDLM LPMSGNIIAS SYARAFQLKD GSFYTAEVKN NIDFKNPIHE  180
SFSKSGPMFT HRRVEETHTK ENLAMVEYQQ VFNSAPRDM                        219
``` as its full-length amino acid sequence, a wild-type plant used in the process for generation of the aimed transformed plant capable of emitting fluorescence is a plant which is capable of undergoing *Agrobacterium* infection and producing a harvestable T1 seed through the self-pollination of each plant individual, and the process for generation of the aimed transformed plant capable of emitting fluorescence comprises the steps of:

inserting a DNA fragment encoding the full-length amino acid sequence of the *Chiridius poppei*-derived fluorescent protein into the cloning site of a T-DNA-based binary vector;

introducing the obtained T-DNA-based binary vector into a host bacterium of the genus *Agrobacterium* such that the bacterium of the genus *Agrobacterium* is transformed therewith;

infecting the wild-type plant with the obtained transformant of the bacterium of the genus *Agrobacterium* such that a T-DNA region contained in the T-DNA-based binary vector is recombinantly introduced in the chromosomal DNA of the wild-type plant to obtain a transformed plant;

subjecting each individual of the obtained transformed plant to self-pollination, and then harvesting a T1 seed from the plant individual; and sowing the obtained T1 seed and screening each grown plant to select a transformed plant individual to which a fluorescent phenotype attributed to the recombinant expression of the fluorescent protein in the leaf surface of the plant has been imparted.

16. The process for generation of the transformed plant capable of emitting fluorescence according to claim 15, wherein a garden plant which is capable of undergoing *Agrobacterium* infection and producing a harvestable T1 seed through the self-pollination of each plant individual is selected as the wild-type plant used in the process for generation of the aimed transformed plant capable of emitting fluorescence.

* * * * *

UNITED STATES PATENT AND TRADEMARK OFFICE
CERTIFICATE OF CORRECTION

PATENT NO. : 8,203,032 B2  
APPLICATION NO. : 12/374995  
DATED : June 19, 2012  
INVENTOR(S) : Iwao Waga, Hiromi Takenaka and Shu Muto Page 1 of 1

It is certified that error appears in the above-identified patent and that said Letters Patent is hereby corrected as shown below:

In the Specifications:

Column 4, Line 21: delete "$\mu_{em.}$" and insert -- $\lambda_{em.}$ --

Column 6, Line 59: delete "SFCMGYGFYII" and insert -- SIICMGYGFYII --

Column 7, Line 7: delete "AGA" and insert -- ACA --

In the Claims:

Column 55, Line 31: In Claim 2, delete "GAG" and insert -- GAC --

Column 57, Line 11: In Claim 4, delete "628" and insert -- 528 --

Signed and Sealed this  
Third Day of September, 2013

Teresa Stanek Rea  
*Acting Director of the United States Patent and Trademark Office*

```
                        SEQUENCE LISTING

<160> NUMBER OF SEQ ID NOS: 17

<210> SEQ ID NO 1
<211> LENGTH: 219
<212> TYPE: PRT
<213> ORGANISM: Chiridius poppei

<400> SEQUENCE: 1

Met Thr Thr Phe Lys Ile Glu Ser Arg Ile His Gly Asn Leu Asn Gly
  1               5                  10                  15

Glu Lys Phe Glu Leu Val Gly Gly Gly Val Gly Glu Glu Gly Arg Leu
             20                  25                  30

Glu Ile Glu Met Lys Thr Lys Asp Lys Pro Leu Ala Phe Ser Pro Phe
         35                  40                  45

Leu Leu Ser His Cys Met Gly Tyr Gly Phe Tyr His Phe Ala Ser Phe
     50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 2
<211> LENGTH: 660
<212> TYPE: DNA
<213> ORGANISM: Chiridius poppei

<400> SEQUENCE: 2 atg aca acc ttc aaa atc gag tcc cgg atc cat ggc aac ctc aac ggg      48
Met Thr Thr Phe Lys Ile Glu Ser Arg Ile His Gly Asn Leu Asn Gly
  1               5                  10                  15 gag aag ttc gag ttg gtt gga ggt gga gta ggt gag gag ggt cgc ctc      96
Glu Lys Phe Glu Leu Val Gly Gly Gly Val Gly Glu Glu Gly Arg Leu
             20                  25                  30 gag att gag atg aag act aaa gat aaa cca ctg gca ttc tct ccc ttc     144
Glu Ile Glu Met Lys Thr Lys Asp Lys Pro Leu Ala Phe Ser Pro Phe
         35                  40                  45
```

```
ctg ctg tcc cac tgc atg ggt tac ggg ttc tac cac ttc gcc agc ttc    192
Leu Leu Ser His Cys Met Gly Tyr Gly Phe Tyr His Phe Ala Ser Phe
    50                  55                  60 cca aag ggg act aag aac atc tat ctt cat gct gca aca aac gga ggt    240
Pro Lys Gly Thr Lys Asn Ile Tyr Leu His Ala Ala Thr Asn Gly Gly
65                  70                  75                  80 tac acc aac acc agg aag gag atc tat gaa gac ggc ggc atc ttg gag    288
Tyr Thr Asn Thr Arg Lys Glu Ile Tyr Glu Asp Gly Gly Ile Leu Glu
                85                  90                  95 gtc aac ttc cgt tac act tac gag ttc aac aag atc atc ggt gac gtc    336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac    384
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc    432
Thr Ile Val Lys Ser Cys Pro Thr Val Asp Leu Met Leu Pro Met Ser
    130                 135                 140 ggg aac atc atc gcc agc tcc tac gct aga gcc ttc caa ctg aag gac    480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat    528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga    576
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac    624
Arg Val Glu Glu Thr His Thr Lys Glu Asn Leu Ala Met Val Glu Tyr
        195                 200                 205 cag cag gtt ttc aac agc gcc cca aga gac atg tag                    660
Gln Gln Val Phe Asn Ser Ala Pro Arg Asp Met  *
    210                 215
```

<210> SEQ ID NO 3
<211> LENGTH: 219
<212> TYPE: PRT
<213> ORGANISM: Artificial Sequence
<220> FEATURE:
<223> OTHER INFORMATION: Synthetic fluorescent protein CpYGFP-H52F

<400> SEQUENCE: 3

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Phe Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140
```

```
Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
            165                 170                 175

Pro Ile His Glu Ser Phe Ser Lys Ser Gly Pro Met Phe Thr His Arg
        180                 185                 190

Arg Val Glu Glu Thr His Thr Lys Glu Asn Leu Ala Met Val Glu Tyr
    195                 200                 205

Gln Gln Val Phe Asn Ser Ala Pro Arg Asp Met
    210                 215

<210> SEQ ID NO 4
<211> LENGTH: 660
<212> TYPE: DNA
<213> ORGANISM: Artificial Sequence
<220> FEATURE:
<223> OTHER INFORMATION: Synthetic DNA construct encoding modified
      fluorescent protein CpYGFP-H52F

<400> SEQUENCE: 4
```

| | | | | | | | | | | | | | | | | |
|---|---|---|---|---|---|---|---|---|---|---|---|---|---|---|---|---|
| atg | aca | acc | ttc | aaa | atc | gag | tcc | cgg | atc | cat | ggc | aac | ctc | aac | ggg | 48 |
| Met | Thr | Thr | Phe | Lys | Ile | Glu | Ser | Arg | Ile | His | Gly | Asn | Leu | Asn | Gly | |
| 1 | | | | 5 | | | | | 10 | | | | | 15 | | |
| gag | aag | ttc | gag | ttg | gtt | gga | ggt | gga | gta | ggt | gag | gag | ggt | cgc | ctc | 96 |
| Glu | Lys | Phe | Glu | Leu | Val | Gly | Gly | Gly | Val | Gly | Glu | Glu | Gly | Arg | Leu | |
| | | | 20 | | | | | 25 | | | | | 30 | | | |
| gag | att | gag | atg | aag | act | aaa | gat | aaa | cca | ctg | gca | ttc | tct | ccc | ttc | 144 |
| Glu | Ile | Glu | Met | Lys | Thr | Lys | Asp | Lys | Pro | Leu | Ala | Phe | Ser | Pro | Phe | |
| | | 35 | | | | | 40 | | | | | 45 | | | | |
| ctg | ctg | tcc | ttc | tgc | atg | ggt | tac | ggg | ttc | tac | cac | ttc | gcc | agc | ttc | 192 |
| Leu | Leu | Ser | Phe | Cys | Met | Gly | Tyr | Gly | Phe | Tyr | His | Phe | Ala | Ser | Phe | |
| | 50 | | | | | 55 | | | | | 60 | | | | | |
| cca | aag | ggg | act | aag | aac | atc | tat | ctt | cat | gct | gca | aca | aac | gga | ggt | 240 |
| Pro | Lys | Gly | Thr | Lys | Asn | Ile | Tyr | Leu | His | Ala | Ala | Thr | Asn | Gly | Gly | |
| 65 | | | | | 70 | | | | | 75 | | | | | 80 | |
| tac | acc | aac | acc | agg | aag | gag | atc | tat | gaa | gac | ggc | ggc | atc | ttg | gag | 288 |
| Tyr | Thr | Asn | Thr | Arg | Lys | Glu | Ile | Tyr | Glu | Asp | Gly | Gly | Ile | Leu | Glu | |
| | | | | 85 | | | | | 90 | | | | | 95 | | |
| gtc | aac | ttc | cgt | tac | act | tac | gag | ttc | aac | aag | atc | atc | ggt | gac | gtc | 336 |
| Val | Asn | Phe | Arg | Tyr | Thr | Tyr | Glu | Phe | Asn | Lys | Ile | Ile | Gly | Asp | Val | |
| | | | 100 | | | | | 105 | | | | | 110 | | | |
| gag | tgc | att | gga | cat | gga | ttc | cca | agt | cag | agt | ccg | atc | ttc | aag | gac | 384 |
| Glu | Cys | Ile | Gly | His | Gly | Phe | Pro | Ser | Gln | Ser | Pro | Ile | Phe | Lys | Asp | |
| | | 115 | | | | | 120 | | | | | 125 | | | | |
| acg | atc | gtg | aag | tcg | tgt | ccc | acg | gtg | gac | ctg | atg | ttg | ccg | atg | tcc | 432 |
| Thr | Ile | Val | Lys | Ser | Cys | Pro | Thr | Val | Asp | Leu | Met | Leu | Pro | Met | Ser | |
| | 130 | | | | | 135 | | | | | 140 | | | | | |
| ggg | aac | atc | atc | gcc | agc | tcc | tac | gct | aga | gcc | ttc | caa | ctg | aag | gac | 480 |
| Gly | Asn | Ile | Ile | Ala | Ser | Ser | Tyr | Ala | Arg | Ala | Phe | Gln | Leu | Lys | Asp | |
| 145 | | | | | 150 | | | | | 155 | | | | | 160 | |
| ggc | tct | ttc | tac | acg | gca | gaa | gtc | aag | aac | aac | ata | gac | ttc | aag | aat | 528 |
| Gly | Ser | Phe | Tyr | Thr | Ala | Glu | Val | Lys | Asn | Asn | Ile | Asp | Phe | Lys | Asn | |
| | | | | 165 | | | | | 170 | | | | | 175 | | |
| cca | atc | cac | gag | tcc | ttc | tcg | aag | tcg | ggg | ccc | atg | ttc | acc | cac | aga | 576 |
| Pro | Ile | His | Glu | Ser | Phe | Ser | Lys | Ser | Gly | Pro | Met | Phe | Thr | His | Arg | |
| | | 180 | | | | | 185 | | | | | 190 | | | | |
| cgt | gtc | gag | gag | act | cac | acc | aag | gag | aac | ctt | gcc | atg | gtg | gag | tac | 624 |
| Arg | Val | Glu | Glu | Thr | His | Thr | Lys | Glu | Asn | Leu | Ala | Met | Val | Glu | Tyr | |
| | 195 | | | | | 200 | | | | | 205 | | | | | |
| cag | cag | gtt | ttc | aac | agc | gcc | cca | aga | gac | atg | tag | | | | | 660 |

```
                    Gln Gln Val Phe Asn Ser Ala Pro Arg Asp Met *
                        210                 215
```

```
<210> SEQ ID NO 5
<211> LENGTH: 782
<212> TYPE: DNA
<213> ORGANISM: Artificial Sequence
<220> FEATURE:
<223> OTHER INFORMATION: Synthetic cDNA encoding fluorescent protein
      CpYGFP from Chiridius poppei

<400> SEQUENCE: 5
```

```
agaacactca gtgtatccag ttttccgtcc tactacaaac                            40 atg aca acc ttc aaa atc gag tcc cgg atc cat ggc aac ctc aac ggg       88
Met Thr Thr Phe Lys Ile Glu Ser Arg Ile His Gly Asn Leu Asn Gly
  1               5                  10                  15 gag aag ttc gag ttg gtt gga ggt gga gta ggt gag gag ggt cgc ctc      136
Glu Lys Phe Glu Leu Val Gly Gly Gly Val Gly Glu Glu Gly Arg Leu
                 20                  25                  30 gag att gag atg aag act aaa gat aaa cca ctg gca ttc tct ccc ttc      184
Glu Ile Glu Met Lys Thr Lys Asp Lys Pro Leu Ala Phe Ser Pro Phe
             35                  40                  45 ctg ctg tcc cac tgc atg ggt tac ggg ttc tac cac ttc gcc agc ttc      232
Leu Leu Ser His Cys Met Gly Tyr Gly Phe Tyr His Phe Ala Ser Phe
         50                  55                  60 cca aag ggg act aag aac atc tat ctt cat gct gca aca aac gga ggt      280
Pro Lys Gly Thr Lys Asn Ile Tyr Leu His Ala Ala Thr Asn Gly Gly
 65                  70                  75                  80 tac acc aac acc agg aag gag atc tat gaa gac ggc ggc atc ttg gag      328
Tyr Thr Asn Thr Arg Lys Glu Ile Tyr Glu Asp Gly Gly Ile Leu Glu
                 85                  90                  95 gtc aac ttc cgt tac act tac gag ttc aac aag atc atc ggt gac gtc      376
Val Asn Phe Arg Tyr Thr Tyr Glu Phe Asn Lys Ile Ile Gly Asp Val
                100                 105                 110 gag tgc att gga cat gga ttc cca agt cag agt ccg atc ttc aag gac      424
Glu Cys Ile Gly His Gly Phe Pro Ser Gln Ser Pro Ile Phe Lys Asp
            115                 120                 125 acg atc gtg aag tcg tgt ccc acg gtg gac ctg atg ttg ccg atg tcc      472
Thr Ile Val Lys Ser Cys Pro Thr Val Asp Leu Met Leu Pro Met Ser
130                 135                 140 ggg aac atc atc gcc agc tcc tac gct aga gcc ttc caa ctg aag gac      520
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat      568
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga      616
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac      664
Arg Val Glu Glu Thr His Thr Lys Glu Asn Leu Ala Met Val Glu Tyr
        195                 200                 205 cag cag gtt ttc aac agc gcc cca aga gac atg tag                      700
Gln Gln Val Phe Asn Ser Ala Pro Arg Asp Met *
    210                 215 aatgtggaac gaaaccttt tttctgatta ctttctctgt tgactccaca               750
ttcggaactt gtataaataa gttcagttta aa                                  782
```

```
<210> SEQ ID NO 6
<211> LENGTH: 30
<212> TYPE: DNA
```

<213> ORGANISM: Artificial Sequence
<220> FEATURE:
<223> OTHER INFORMATION: Synthetic oligonucletide primer

<400> SEQUENCE: 6

```
ttc tgc atg ggt tac ggg ttc tac cac ttc                    30
Phe Cys Met Gly Tyr Gly Phe Tyr His Phe
 1               5                  10
```

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucletide primer

<400> SEQUENCE: 7
ggacagcagg aagggagaga atgccagt                              28

<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucletide primer

<400> SEQUENCE: 8
caccatgaca accttcaaaa tcgagtcc                              28

<210> SEQ ID NO 9
<211> LENGTH: 35
<212> TYPE: DNA
<213> ORGANISM: Artificial Sequence
<220> FEATURE:
<223> OTHER INFORMATION: Synthetic oligonucletide primer

<400> SEQUENCE: 9
ctcgtcgacc tacatgtctc ttggggcgct gttga                      35

<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucletide primer

<400> SEQUENCE: 10
gtacgtattt ttacaacaat taccaac                               27

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucletide primer

<400> SEQUENCE: 11
ggattcaatc ttaagaaact ttattgc                               27

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucletide primer

<400> SEQUENCE: 12

```
actggcattc tctcccttcc tgctgtcc                                              28
```

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucletide primer

<400> SEQUENCE: 13

```
tgaccgtaag agagggaagg acgacagg                                              28
```

<210> SEQ ID NO 14
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 14

```
Leu Ala Phe Ser Pro Phe Leu Leu Ser
 1               5
```

<210> SEQ ID NO 15
<211> LENGTH: 782
<212> TYPE: DNA
<213> ORGANISM: Artificial Sequence
<220> FEATURE:
<223> OTHER INFORMATION: Synthetic cDNA encoding fluorescent protein
      H52F CpYGFP

<400> SEQUENCE: 15

```
agaacactca gtgtatccag ttttccgtcc tactacaaac                                 40 atg aca acc ttc aaa atc gag tcc cgg atc cat ggc aac ctc aac ggg            88
Met Thr Thr Phe Lys Ile Glu Ser Arg Ile His Gly Asn Leu Asn Gly
 1               5                  10                  15 gag aag ttc gag ttg gtt gga ggt gga gta ggt gag gag ggt cgc ctc            136
Glu Lys Phe Glu Leu Val Gly Gly Gly Val Gly Glu Glu Gly Arg Leu
                20                  25                  30 gag att gag atg aag act aaa gat aaa cca ctg gca ttc tct ccc ttc            184
Glu Ile Glu Met Lys Thr Lys Asp Lys Pro Leu Ala Phe Ser Pro Phe
            35                  40                  45 ctg ctg tcc ttc tgc atg ggt tac ggg ttc tac cac ttc gcc agc ttc            232
Leu Leu Ser Phe Cys Met Gly Tyr Gly Phe Tyr His Phe Ala Ser Phe
        50                  55                  60 cca aag ggg act aag aac atc tat ctt cat gct gca aca aac gga ggt            280
Pro Lys Gly Thr Lys Asn Ile Tyr Leu His Ala Ala Thr Asn Gly Gly
 65                  70                  75                  80 tac acc aac acc agg aag gag atc tat gaa gac ggc ggc atc ttg gag            328
Tyr Thr Asn Thr Arg Lys Glu Ile Tyr Glu Asp Gly Gly Ile Leu Glu
                85                  90                  95 gtc aac ttc cgt tac act tac gag ttc aac aag atc atc ggt gac gtc            376
Val Asn Phe Arg Tyr Thr Tyr Glu Phe Asn Lys Ile Ile Gly Asp Val
                100                 105                 110 gag tgc att gga cat gga ttc cca agt cag agt ccg atc ttc aag gac            424
Glu Cys Ile Gly His Gly Phe Pro Ser Gln Ser Pro Ile Phe Lys Asp
            115                 120                 125 acg atc gtg aag tcg tgt ccc acg gtg gac ctg atg ttg ccg atg tcc            472
Thr Ile Val Lys Ser Cys Pro Thr Val Asp Leu Met Leu Pro Met Ser
        130                 135                 140 ggg aac atc atc gcc agc tcc tac gct aga gcc ttc caa ctg aag gac            520
Gly Asn Ile Ile Ala Ser Ser Tyr Ala Arg Ala Phe Gln Leu Lys Asp
145                 150                 155                 160
```

| | | | | | | | | | | | | | | | | |
|---|---|---|---|---|---|---|---|---|---|---|---|---|---|---|---|---|
|ggc|tct|ttc|tac|acg|gca|gaa|gtc|aag|aac|aac|ata|gac|ttc|aag|aat|568|
|Gly|Ser|Phe|Tyr|Thr|Ala|Glu|Val|Lys|Asn|Asn|Ile|Asp|Phe|Lys|Asn| |
| | | |165| | | |170| | | |175| | | | | |

| | | | | | | | | | | | | | | | | |
|---|---|---|---|---|---|---|---|---|---|---|---|---|---|---|---|---|
|cca|atc|cac|gag|tcc|ttc|tcg|aag|tcg|ggg|ccc|atg|ttc|acc|cac|aga|616|
|Pro|Ile|His|Glu|Ser|Phe|Ser|Lys|Ser|Gly|Pro|Met|Phe|Thr|His|Arg| |
| | |180| | | | |185| | | | |190| | | | |

| | | | | | | | | | | | | | | | | |
|---|---|---|---|---|---|---|---|---|---|---|---|---|---|---|---|---|
|cgt|gtc|gag|gag|act|cac|acc|aag|gag|aac|ctt|gcc|atg|gtg|gag|tac|664|
|Arg|Val|Glu|Glu|Thr|His|Thr|Lys|Glu|Asn|Leu|Ala|Met|Val|Glu|Tyr| |
| | |195| | | |200| | | |205| | | | | | |

| | | | | | | | | | |
|---|---|---|---|---|---|---|---|---|---|
|cag|cag|gtt|ttc|aac|agc|gcc|cca|aga|gac|atg|tag|700|
|Gln|Gln|Val|Phe|Asn|Ser|Ala|Pro|Arg|Asp|Met|*| |
| |210| | | |215| | | | | | | | aatgtggaac gaaacctttt tttctgatta ctttctctgt tgactccaca        750 ttcggaactt gtataaataa gttcagttta aa                            782

```
<210> SEQ ID NO 16
<211> LENGTH: 225
<212> TYPE: PRT
<213> ORGANISM: Artificial Sequence
<220> FEATURE:
<223> OTHER INFORMATION: Synthetic DsRed fluorescent protein

<400> SEQUENCE: 16
```

Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gly Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

```
<210> SEQ ID NO 17
<211> LENGTH: 238
<212> TYPE: PRT
<213> ORGANISM: Artificial Sequence
```

-continued

<220> FEATURE:
<223> OTHER INFORMATION: Synthetic aqGFP fluorescent protein

<400> SEQUENCE: 17

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Glu Gln Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235
```